United States Patent
Zhai et al.

(10) Patent No.: US 12,233,047 B2
(45) Date of Patent: Feb. 25, 2025

(54) PHARMACEUTICAL COMBINATION AND USE THEREOF

(71) Applicants: ASCENTAGE PHARMA (SUZHOU) CO., LTD., Suzhou (CN); ASCENTAGE PHARMA GROUP CORP LIMITED, Central (CN); GUANGZHOU HEALTHQUEST PHARMA CO., LTD., Guangzhou (CN)

(72) Inventors: Yifan Zhai, Suzhou (CN); Dajun Yang, Suzhou (CN); Douglas Dong Fang, Suzhou (CN); Qiuqiong Tang, Suzhou (CN)

(73) Assignees: ASCENTAGE PHARMA (SUZHOU) CO., LTD. (CN); ASCENTAGE PHARMA GROUP CORP LIMITED (CN)

( * ) Notice: Subject to any disclaimer, the term of this patent is extended or adjusted under 35 U.S.C. 154(b) by 378 days.

(21) Appl. No.: 17/421,131

(22) PCT Filed: Jul. 16, 2020

(86) PCT No.: PCT/CN2020/102275
§ 371 (c)(1),
(2) Date: Jul. 7, 2021

(87) PCT Pub. No.: WO2021/013028
PCT Pub. Date: Jan. 28, 2021

(65) Prior Publication Data
US 2022/0142975 A1   May 12, 2022

(30) Foreign Application Priority Data

Jul. 19, 2019   (WO) ................ PCT/CN2019/096843
Jun. 28, 2020   (CN) ......................... 202010598136.2

(51) Int. Cl.
*A61K 31/403*   (2006.01)
*A61K 31/437*   (2006.01)
*A61P 35/02*    (2006.01)

(52) U.S. Cl.
CPC .......... *A61K 31/403* (2013.01); *A61K 31/437* (2013.01); *A61P 35/02* (2018.01)

(58) Field of Classification Search
CPC .................................................. A61K 31/403
See application file for complete search history.

(56) References Cited

FOREIGN PATENT DOCUMENTS

| CA | 2804347 A1 * | 1/2012 |
| CN | 111035641 A1 | 4/2020 |
| WO | WO2012000304 A1 | 1/2012 |
| WO | WO 2015/161032 A1 * | 10/2015 |

OTHER PUBLICATIONS

Lala, et al. Cancer and Metastasis Reviews (1998), 17(1),91-106.*
Golub, et al. Science 286, 531(1999).*
Cancer [online], [retrieved on Aug. 11, 2023]. Retrieved from the internet, URLhttps://medlineplus.gov/cancer.html#>.*
Ren, X et al., "Identification of GZD824 as an Orally Bioavailable Inhibitor That Targets Phosphorylated and Nonphosphorylated Breakpoint Cluster Region-Abelson (Bcr-Abl) Kinase and Overcomes Clinically Acquired Mutation-Induced Resistance Against Imatinib". Journal of Medical Chemistry, vol. 56, No. 3, Jan. 9, 2013 (Jan. 9, 2013); pp. 879-894.
Gozgit, J.M., et al. "Potent Activity of Ponatinib (AP24534) in Models of FLT3-Driven Acute Myeloid Leukemia and Other Hematological Malignancies." Molecular Cancer Therapeutics, vol. 10, No. 6, Apr. 11, 2011 (Apr. 11, 2011), ISSN: 1538-8514; pp. 1028-1035.
Oct. 27, 2020 International Search Report for PCT/CN2020/102275, 4 pages.

* cited by examiner

*Primary Examiner* — Shawquia Jackson
(74) *Attorney, Agent, or Firm* — Honigman LLP; Lucy X. Yang; Jonathan P. O'Brien

(57) ABSTRACT

The invention discloses a novel pharmaceutical combination and a use thereof. The pharmaceutical combination comprises a compound of formula (I), a pharmaceutically acceptable salt thereof or a solvate thereof; and a compound of formula (II), a pharmaceutically acceptable salt thereof or a solvate thereof. The pharmaceutical combination can be used to treat cancer.

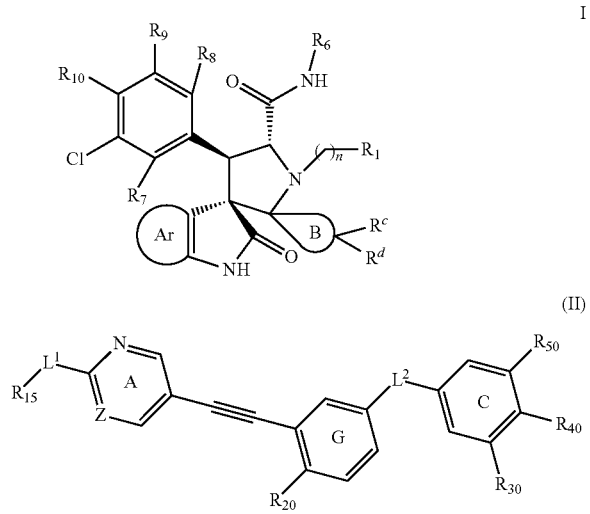

20 Claims, 2 Drawing Sheets

PHARMACEUTICAL COMBINATION AND USE THEREOF

CROSS-REFERENCE TO RELATED APPLICATIONS

This application is a 35 U.S.C. § 371 United States National Phase Application and claims the benefit of International patent application PCT/CN2020/102275 filed Jul. 16, 2020, which claims the benefit of International patent application PCT/CN2019/096843 filed on Jul. 19, 2019 and Chinese patent application CN202010598136.2 filed on Jun. 28, 2020. The contents of which are incorporated herein by reference in their entireties.

FIELD OF THE INVENTION

The invention relates to a pharmaceutical composition and use thereof. The invention also relates to a combination therapy involving a MDM2 inhibitor and a FLT3-inhibitors for the treatment of a patient suffering from cancer, particular a cancer with internal tandem duplication of the FLT3 gene.

BACKGROUND OF THE INVENTION

Targeting the p53 antagonist MDM2 is a novel approach to restore the crucial p53 tumor suppressor function in AML cells (Kojima K, Konopleva M, Samudio I J, et al. *Blood*. 2005, 106(9): 3150-3159). Acute myeloid leukemia (AML) is one of the most common types of leukemia among adults. The past decade has witnessed major advances in our comprehension of the biologic heterogeneity of AML.

An internal tandem duplication (ITD) of FLT3 (Fms-like tyrosine kinase 3) gene has been found in AML (Kiyoi etc., H Internal tandem duplication (ITD) of FLT3 gene is a novel modality of elongation mutation which causes constitutive activation of the product, *Leukemia* (1998) 12, 1333-1337). In internal tandem duplication of FLT3 gene, a fragment of the JM domain-coding sequence, which primarily consists of exon 11 but sometimes includes intron 11 and exon 12, is arranged as a direct head-to-tail sequence. An internal tandem duplication of the FLT3 gene accounts for nearly 20% of acute myeloid leukemia (AML), and their prognosis is poor, particularly in unfit, refractory or relapsed patients, thus highlighting an unmet need for novel therapeutic approaches. Mutations within the tyrosine kinase domain (TKD) are the second most common type of FLT3 mutation in AML (occurring in up to 14% of adult patients with AML). Mutations within the TKD are primarily point mutations within the activation loop (e.g., residues D835, I836, and Y842) of the TKD2 and, to a lesser extent, within the TKD1 (e.g., residues N676 and F691). Other point mutations and smaller insertions/deletions have also been identified within the TKD and other domains (e.g., extracellular and juxtamembrane domains (occurring in about 2% of patients with AML)). The prognostic significance of FLT3-TKD mutations in the overall AML population and the impact of the FLT3-TKD allelic ratio are still debatable and may depend on additional mutations as well as the cytogenetic background (Patnaik etc., The importance of FLT3 mutational analysis in acute myeloid leukemia, Leukemia & Lymphoma (2018) 59, 2273-2286). FLT3 kinase is part of a family of proteins called receptor tyrosine kinases (RTKs). WO2012000304A1 (also published as EP2594567A1, US2013196985A1 and so on) discloses a series of heterocyclic benzene compounds of protein tyrosine kinase which have advanced into clinical trial, and some of them have been approved for clinical use and achieved excellent therapeutic effect. However, the indications response to cancer therapy still remains a challenge. There is a continuing need for development of inhibitors on cancer treatment.

SUMMARY OF THE INVENTION

The invention relates to a novel pharmaceutical combination and use thereof.

In one aspect, the invention provides a pharmaceutical combination comprising:

substance M, wherein the substance M is a compound of formula (I), a pharmaceutically acceptable salt thereof or a solvate thereof; and substance N, wherein the substance N is a compound of formula (II), a pharmaceutically acceptable salt thereof or a solvate thereof;

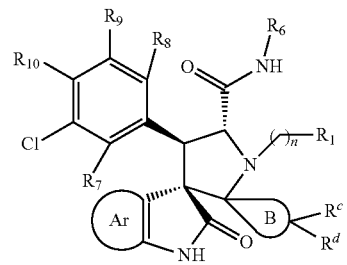

I wherein,

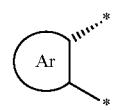

is selected from the group consisting of

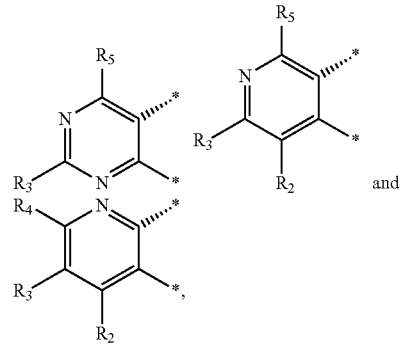

and ring B is a $C_{4-7}$ carbocyclic ring;

$R_1$ is H, substituted or unsubstituted $C_{1-4}$ alkyl, substituted or unsubstituted $C_{3-8}$ cycloalkyl, substituted or unsubstituted 4 to 12-membered heterocycloalkyl, $OR^a$, or $NR^aR^b$; the heteroatom of the heterocycloalkyl is independently selected from the group consisting of nitrogen, oxygen and sulfur, the number of the heteroatom is 1 to 4;

n is 0, 1, or 2;

$R_2$, $R_3$, $R_4$, $R_5$, $R_7$, $R_8$, $R_9$, and $R_{10}$ are independently selected from the group consisting of H, F, Cl, $CH_3$ and $CF_3$;

$R_6$ is

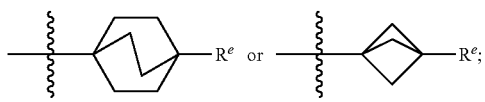

each of $R^a$ is independently H, or substituted or unsubstituted $C_{1-4}$ alkyl;

each of $R^b$ is independently H, or substituted or unsubstituted $C_{1-4}$ alkyl;

$R^c$ and $R^d$ are substituents on one carbon atom of ring B, wherein $R^c$ is H, $C_{1-3}$ alkyl, $C_{1-3}$ alkylene-$OR^a$, $OR^a$, or halogen;

$R^d$ is H, $C_{1-3}$ alkyl, $C_{1-3}$ alkylene-$OR^a$, $OR^a$, or halogen;

or, $R^c$ and $R^d$ are taken together with the carbon to which they are attached to form a 4 to 6-membered spiro substituent, optionally containing an oxygen atom;

$R^e$ is —C(=O)$OR^a$, —C(=O)$NR^aR^b$, or —C(=O)NHSO$_2$CH$_3$;

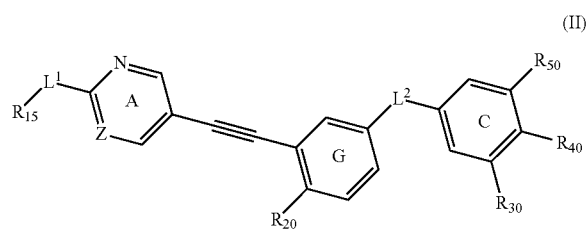

(II)

wherein Z is CH or N;

$L^1$ is NH, —N= or CH;

$L^2$ is —CONH— or —NHCO—;

$R_{15}$ is H, $C_{1-6}$ alkyl, $C_{3-6}$ cycloalkyl, $C_{1-5}$ alkyl substituted by one or two hydroxyl, or phenyl;

or, $R_{15}$ together with $L^1$, the carbon to which $L^1$ is attached, Z and ring A form a moiety having the structure

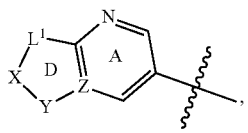

wherein $L^1$ is NH, —N= or CH; X, Y and Z are independently N or CH; ring D is an aromatic heterocycle containing 1 to 3 nitrogen atom(s);

$R_{20}$ is H, halogen (e.g., F, Cl or Br), $C_{1-5}$ alkyl, $C_{3-6}$ cycloalkyl, or $C_{1-5}$ alkyl substituted by one or more F;

$R_{30}$ is H, halogen (e.g., F, Cl or Br), $C_{1-4}$ alkyl, $C_{3-6}$ cycloalkyl, or $C_{1-4}$ alkyl substituted by one or more F;

$R_{50}$ is H, provide that $R_{40}$ is H, (CH$_2$)$_m$NR$_{60}$R$_{70}$ or (CH$_2$)$_m$Het$^1$;

$R_{40}$ is H, provide that $R_{50}$ is H or (CH$_2$)$_m$Het$^2$;

each of m is independently 0 or 1;

Het$^1$ is a nonaromatic heterocycle containing 1 to 3 nitrogen atoms; Het$^2$ is an aromatic 5-6 membered heterocycle containing 1 to 3 heteroatom(s) independently selected from the group consisting of nitrogen, oxygen and sulfur; wherein any carbon or nitrogen atom of Het$^1$ and Het$^2$ is optionally substituted by alkyl, alkyl substituted by one or more hydroxyl, cycloalkyl or NR$_{60}$R$_{70}$;

each of $R_{60}$ and $R_{70}$ is independently H, $C_{1-3}$ alkyl, $C_{1-3}$ alkyl substituted by one or more F, or $C_{3-6}$ cycloalkyl;

or, $R_{60}$ and $R_{70}$ can further form penta-, hexa-, hepta- or octa-tomic ring structure through C, O, N, S atoms (e.g., $R_{60}$ and $R_{70}$ together with the nitrogen atom to which they are attached form a penta-, hexa-, hepta- or octa-tomic ring (e.g., the ring is a heterocycloalkyl), wherein the penta-, hexa-, hepta- or octa-tomic ring optionally further contains an oxygen or sulfur atom).

In some embodiments,

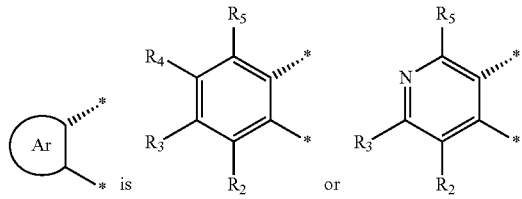

In some embodiments, ring B is

In some embodiments, ring B, $R^c$ are taken together with $R^d$ to form

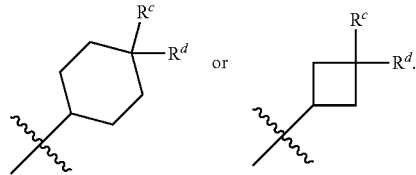

In some embodiments, $R^c$ and $R^d$ are independently H, halogen, OH, CH$_3$, CH$_2$CH$_3$, or CH$_2$OH. In some embodiments, $R^c$ and $R^d$ are F and F; H and H; OH and CH$_3$; OH and H; CH$_3$ and CH$_3$; CH$_3$ and OH; H and OH; CH$_2$CH$_3$ and CH$_2$CH$_3$; or, CH$_2$OH and CH$_2$OH.

In some embodiments, $R^c$ and $R^d$ are taken together with ring B to form a spiro moiety selected from the group consisting of

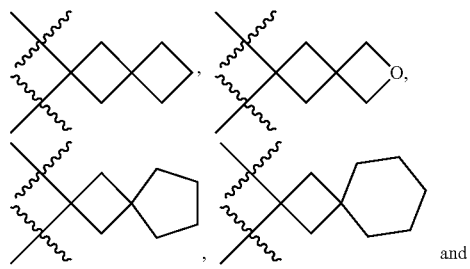

and

-continued

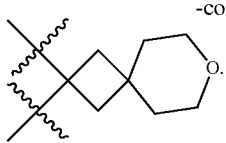

In some embodiments, R$^c$ and R$^d$ are taken together with ring B to form

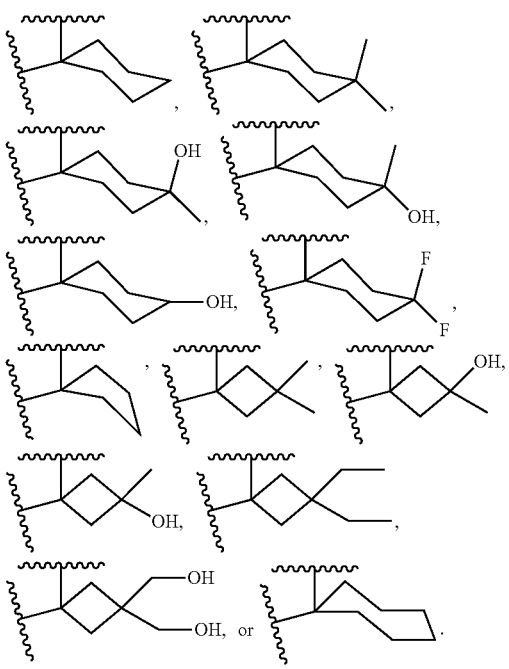

In some embodiments, R$^a$ and R$^b$ are independently H, CH$_3$, or CH$_2$CH$_3$.

In some embodiments, R$^6$ is

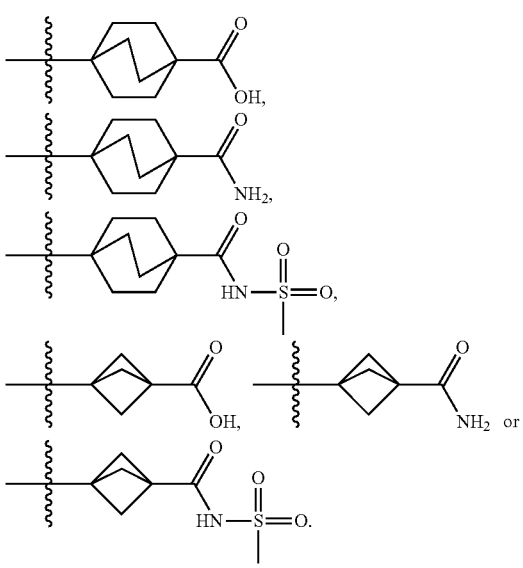

In some embodiments, n is 0 or 1.
In some embodiments, R$_1$ is H or CH$_3$.

In some embodiments,

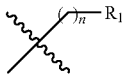

is H, CH$_3$, or CH$_2$CH$_3$.

In some embodiments, R$_2$ is H.
In some embodiments, R$_4$ is H.
In some embodiments, R$_5$ is H.
In some embodiments, R$_3$ is halogen, preferably Cl.
In some embodiments, R$_4$ and R$_5$ are H.
In some embodiments, R$_7$ is F.
In some embodiments, each of R$_8$, R$_9$, and R$_{10}$ is H.
In some embodiments, R$^e$ is —C(=O)OH, —C(=O)NH$_2$, or —C(=O)NHSO$_2$CH$_3$.

In some embodiments, the compound of formula (I) is selected from the group consisting of Compound Q

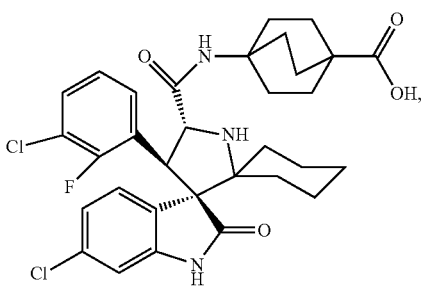

Compound M

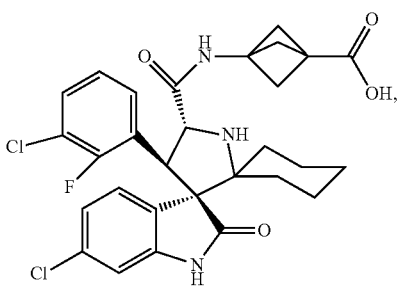

Compound N

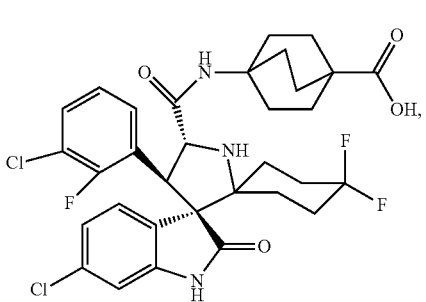

-continued
Compound H
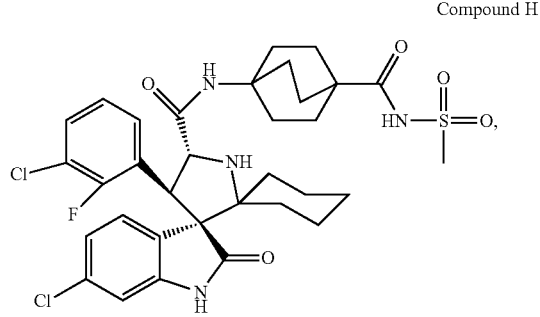
Compound J
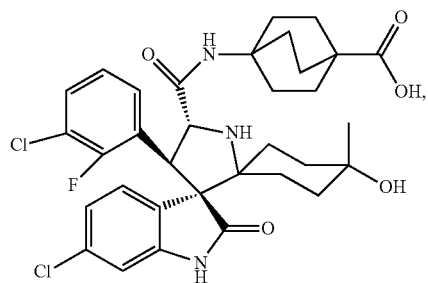
Compound G
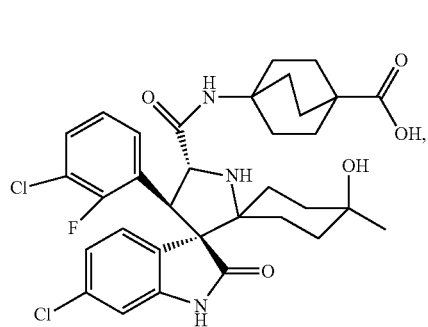
Compound E
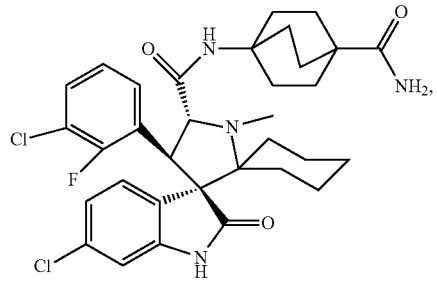
Compound C
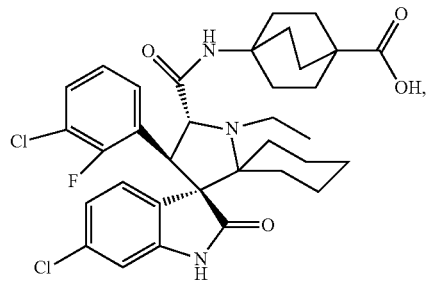
-continued
Compound F
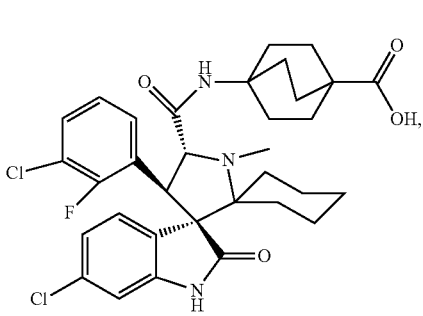
Compound Y
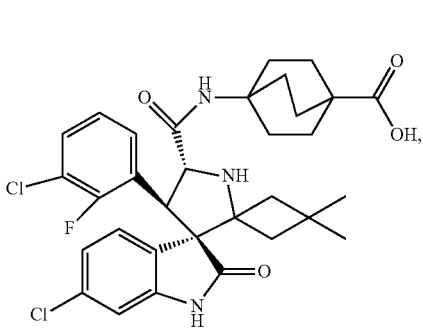
Compound K
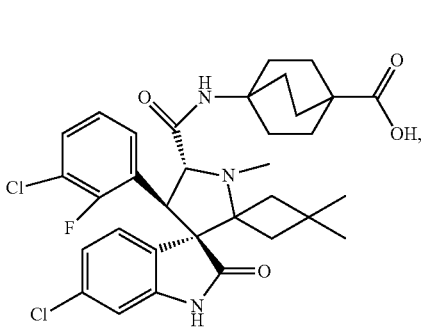
Compound P
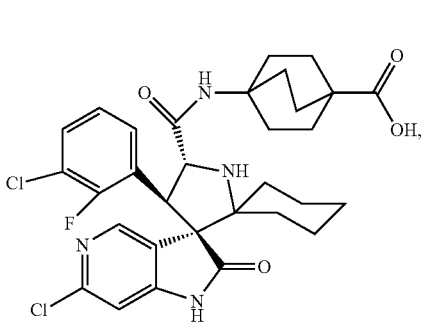
Compound T
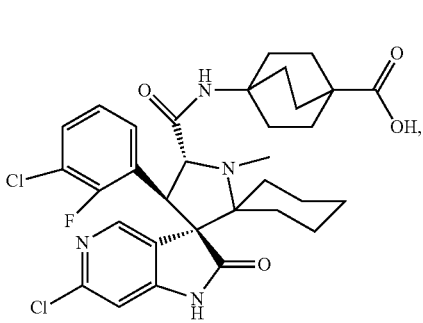

-continued

Compound S

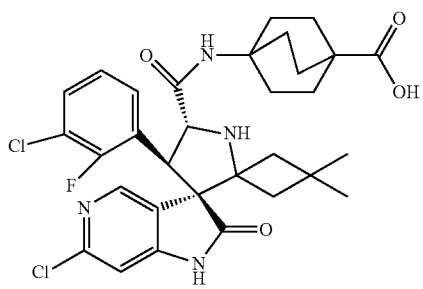

and

Compound W

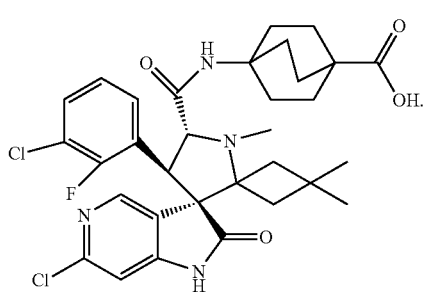

In some embodiments, the compound of formula (I) is Compound C.

In some embodiments, Z is N, $L^1$ is NH, $R_{15}$ is methyl, ethyl, isopropyl, tert-butyl, cyclopropyl, cyclobutyl, cyclopentyl or cyclohexyl.

In some embodiments, $R_{15}$ together with $L^1$, the carbon to which $L^1$ is attached, Z and ring A form a moiety having the structure

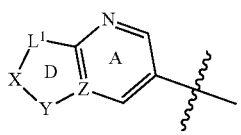

which is selected from the group consisting of

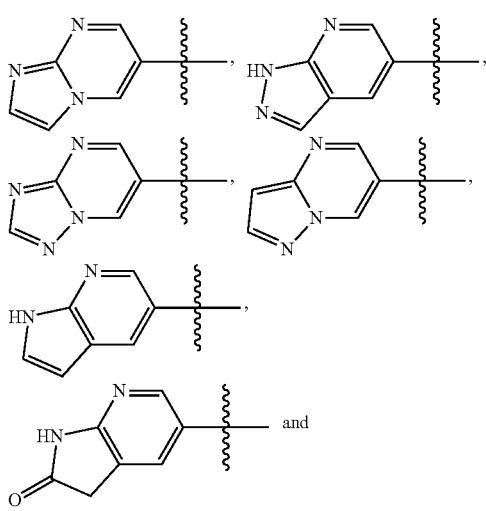

and

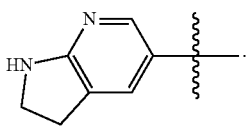

In some embodiments, $R_{20}$ is H, methyl, ethyl, isopropyl, tert-butyl, cyclopropyl, F, Cl, Br or $CF_3$.

In some embodiments, the moiety

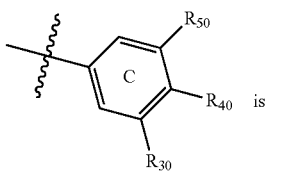

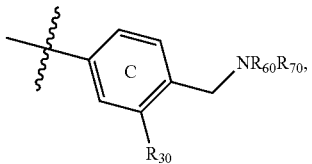

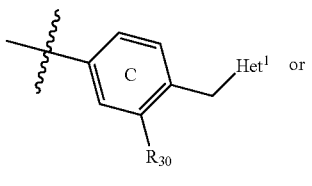

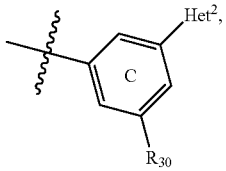

wherein $R_{30}$, $R_{60}$, $R_{70}$ and $Het^1$ are as defined herein, $Het^2$ is substituted imidazole, substituted oxazole, substituted triazole, substituted oxazolidine or substituted thiazole.

In some embodiments, $R_{30}$ is H, F, Cl, $CF_3$ or tert-butyl.

In some embodiments, $R_{40}$ is

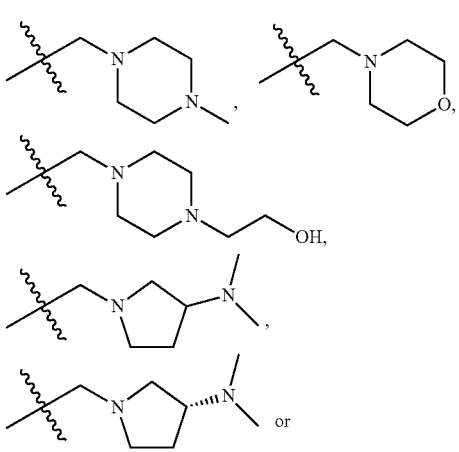

or

-continued

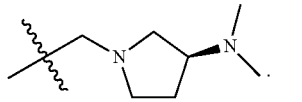

In some embodiments, $R_{50}$ is

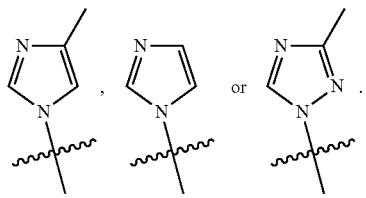

In some embodiments, the compound of formula (II) has a structure selected from the group consisting of (III)
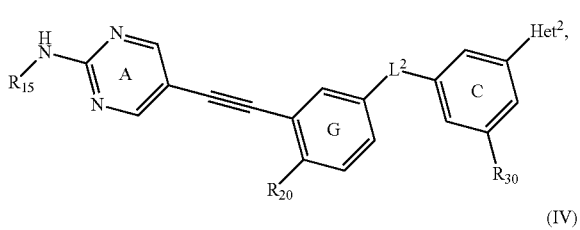

(IV)
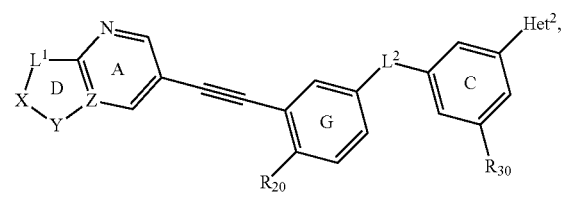

(V)
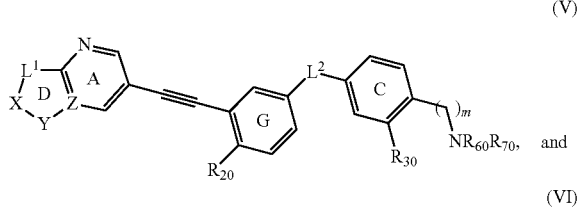

(VI)
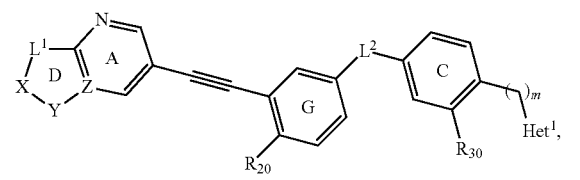

wherein, X, Y and Z are independently N or CH;
D ring contains 1 to 3 nitrogen atoms;
the moiety

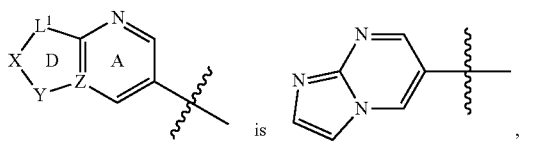 is

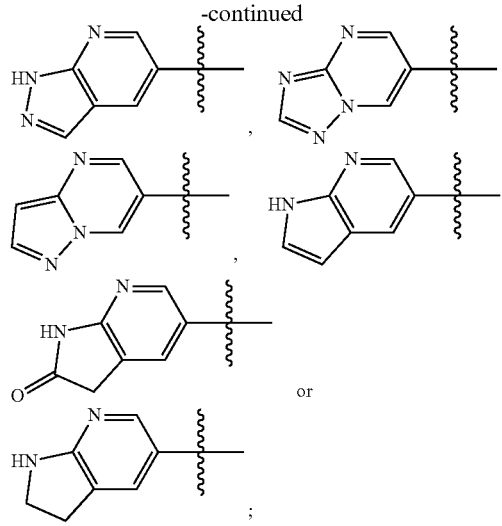

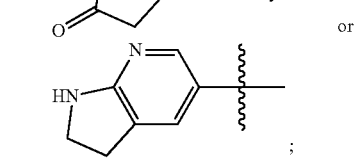

$R_{15}$, $R_{20}$, $R_{30}$, $R_{60}$, $R_{70}$, m, $L^1$, $L^2$, $Het^1$ and $Het^2$ are as defined herein.

In some embodiments, the compound of formula (II) is selected from the group consisting of
3-(2-(2-(cyclopropylamino)pyrimidin-5-yl)ethynyl)-4-methyl-N-(3-(4-methyl-1H-imidazol-1-yl)-5-(trifluoromethyl)phenyl)benzamide (Compound 1);
N-(3-(1H-imidazol-1-yl)-5-(trifluoromethyl)phenyl)-3-(2-(2-(cyclopropylamino)pyrimidin-5-yl)ethynyl)-4-methylbenzamide (Compound 2);
4-methyl-N-(3-(4-methyl-1H-imidazol-1-yl)-5-(trifluoromethyl)phenyl)-3-(2-(2-(methylamino)pyrimidin-5-yl)ethynyl)benzamide (Compound 3);
3-(2-(2-(ethylamino)pyrimidin-5-yl)ethynyl)-4-methyl-N-(3-(4-methyl-1H-imidazol-1-yl)-5-(trifluoromethyl)phenyl)benzamide (Compound 4);
4-methyl-N-(3-(4-methyl-1H-imidazol-1-yl)-5-(trifluoromethyl)phenyl)-3-(2-(2-(piperidin-1-yl)pyrimidin-5-yl)ethynyl)benzamide (Compound 5);
3-(2-(6-aminopyridin-3-yl)ethynyl)-4-methyl-N-(3-(4-methyl-1H-imidazol-1-yl)-5-(trifluoromethyl)phenyl)benzamide (Compound 6);
3-(2-(2-(cyclopropylamino)pyrimidin-5-yl)ethynyl)-4-methyl-N-(4-((4-methylpiperazin-1-yl)methyl)-3-(trifluoromethyl)phenyl)benzamide (Compound 7);
3-(2-(3H-imidazo[4,5-b]pyridin-6-yl)ethynyl)-4-methyl-N-(3-(4-methyl-1H-imidazol-1-yl)-5-(trifluoromethyl)phenyl)benzamide (Compound 8);
4-methyl-N-(4-((4-methylpiperazin-1-yl)methyl)-3-(trifluoromethyl)phenyl)-3-(2-(pyrazolo[1,5-a]pyrimidin-6-yl)ethynyl)benzamide (Compound 9);
3-(2-(2-(cyclohexylamino)pyrimidin-5-yl)ethynyl)-4-methyl-N-(3-(4-methyl-1H-imidazol-1-yl)-5-(trifluoromethyl)phenyl)benzamide (Compound 10);
4-methyl-N-(3-(4-methyl-1H-imidazol-1-yl)-5-(trifluoromethyl)phenyl)-3-(2-(2-(phenylamino)pyrimidin-5-yl)ethynyl)benzamide (Compound 11);
3-(2-(1H-pyrrolo[2,3-b]pyridin-5-yl)ethynyl)-4-methyl-N-(3-(4-methyl-1H-imidazol-1-yl)-5-(trifluoromethyl)phenyl)benzamide (Compound 12);
3-(2-(2-(2-hydroxyethylamino)pyrimidin-5-yl)ethynyl)-4-methyl-N-(3-(4-methyl-1H-imidazol-1-yl)-5-(trifluoromethyl)phenyl)benzamide (Compound 13);
N-(3-(1H-imidazol-1-yl)-5-(trifluoromethyl)phenyl)-4-methyl-3-(2-(pyrazolo[1,5-a]pyrimidin-6-yl)ethynyl)benzamide (Compound 14);

4-methyl-N-(3-(3-methyl-1H-1,2,4-triazol-1-yl)-5-(trifluoromethyl)phenyl)-3-(2-(pyrazolo[1,5-a]pyrimidin-6-yl)ethynyl)benzamide (Compound 15);

3-(2-(imidazo[1,2-a]pyrimidin-6-yl)ethynyl)-4-methyl-N-(3-(4-methyl-1H-imidazol-1-yl)-5-(trifluoromethyl)phenyl)benzamide (Compound 16);

3-(2-(1H-pyrazolo[3,4-b]pyridin-5-yl)ethynyl)-4-methyl-N-(3-(4-methyl-1H-imidazol-1-yl)-5-(trifluoromethyl)phenyl)benzamide (Compound 17);

N-(3-(1H-imidazol-1-yl)-5-(trifluoromethyl)phenyl)-3-(2-(1H-pyrazolo[3,4-b]pyridin-5-yl)ethynyl)-4-methylbenzamide (Compound 18);

3-(2-(1H-pyrazolo[3,4-b]pyridin-5-yl)ethynyl)-4-methyl-N-(3-(3-methyl-1H-1,2,4-triazol-1-yl)-5-(trifluoromethyl)phenyl)benzamide (Compound 19);

3-(2-([1,2,4]triazolo[1,5-a]pyrimidin-6-yl)ethynyl)-4-methyl-N-(3-(4-methyl-1H-imidazol-1-yl)-5-(trifluoromethyl)phenyl)benzamide (Compound 20);

4-methyl-N-(3-(4-methyl-1H-imidazol-1-yl)-5-(trifluoromethyl)phenyl)-3-(2-(pyrazolo[1,5-a]pyrimidin-6-yl)ethynyl)benzamide (Compound 21);

3-(2-(1H-pyrazolo[3,4-b]pyridin-5-yl)ethynyl)-4-methyl-N-(3-(trifluoromethyl)phenyl)benzamide (Compound 22);

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide (Compound 23);

3-(2-(2-((S)-2,3-dihydroxypropylamino)pyrimidin-5-yl)ethynyl)-4-methyl-N-(3-(4-methyl-1H-imidazol-1-yl)-5-(trifluoromethyl)phenyl)benzamide (Compound 24);

3-(2-(2-(diethylamino)pyrimidin-5-yl)ethynyl)-4-methyl-N-(3-(4-methyl-1H-imidazol-1-yl)-5-(trifluoromethyl)phenyl)benzamide (Compound 25);

3-(2-(2-(tert-butylamino)pyrimidin-5-yl)ethynyl)-4-methyl-N-(3-(4-methyl-1H-imidazol-1-yl)-5-(trifluoromethyl)phenyl)benzamide (Compound 26);

3-(2-(2-(isopropylamino)pyrimidin-5-yl)ethynyl)-4-methyl-N-(3-(4-methyl-1H-imidazol-1-yl)-5-(trifluoromethyl)phenyl)benzamide (Compound 27);

3-(2-(2-aminopyrimidin-5-yl)ethynyl)-4-methyl-N-(3-(4-methyl-1H-imidazol-1-yl)-5-(trifluoromethyl)phenyl)benzamide (Compound 28);

4-methyl-N-(4-(morpholinomethyl)-3-(trifluoromethyl)phenyl)-3-(2-(pyrazolo[1,5-a]pyrimidin-6-yl)ethynyl)benzamide (Compound 29);

N-(4-((4-(2-hydroxyethyl)piperazin-1-yl)methyl)-3-(trifluoromethyl)phenyl)-4-methyl-3-(2-(pyrazolo[1,5-a]pyrimidin-6-yl)ethynyl)benzamide (Compound 30);

(S)—N-(4-((3-(dimethylamino)pyrrolidin-1-yl)methyl)-3-(trifluoromethyl)phenyl)-4-methyl-3-(2-(pyrazolo[1,5-a]pyrimidin-6-yl)ethynyl)benzamide (Compound 31);

N-(3-tert-butyl-5-(4-methyl-1H-imidazol-1-yl)phenyl)-4-methyl-3-(2-(pyrazolo[1,5-a]pyrimidin-6-yl)ethynyl)benzamide (Compound 32);

3-(2-(1H-pyrazolo[3,4-b]pyridin-5-yl)ethynyl)-4-methyl-N-(3-(4-methyl-1H-imidazol-1-yl)phenyl)benzamide (Compound 33);

3-(2-(1H-pyrazolo[3,4-b]pyridin-5-yl)ethynyl)-N-(3-tert-butyl-5-(4-methyl-1H-imidazol-1-yl)phenyl)-4-methylbenzamide (Compound 34);

3-(2-(1H-pyrazolo[3,4-b]pyridin-5-yl)ethynyl)-N-(3-fluoro-5-(4-methyl-1H-imidazol-1-yl)phenyl)-4-methylbenzamide (Compound 35);

3-(2-(1H-pyrazolo[3,4-b]pyridin-5-yl)ethynyl)-N-(3-chloro-5-(4-methyl-1H-imidazol-1-yl)phenyl)-4-methylbenzamide (Compound 36);

(R)—N-(4-((3-(dimethylamino)pyrrolidin-1-yl)methyl)-3-(trifluoromethyl)phenyl)-4-methyl-3-(2-(pyrazolo[1,5-a]pyrimidin-6-yl)ethynyl)benzamide (Compound 37);

(S)-3-(2-(1H-pyrazolo[3,4-b]pyridin-5-yl)ethynyl)-N-(4-((3-(dimethylamino)pyrrolidin-1-yl)methyl)-3-(trifluoromethyl)phenyl)-4-methylbenzamide (Compound 38);

(R)-3-(2-(1H-pyrazolo[3,4-b]pyridin-5-yl)ethynyl)-N-(4-((3-(dimethylamino)pyrrolidin-1-yl)methyl)-3-(trifluoromethyl)phenyl)-4-methylbenzamide (Compound 39); and, 3-(2-(1H-pyrazolo[3,4-b]pyridin-5-yl)ethynyl)-N-(4-((4-methylpiperazin-1-yl)methyl)-3-(trifluoromethyl)phenyl)benzamide (Compound 40).

In some embodiments, the pharmaceutically acceptable salt of the compound of formula (II) is formed by the compound of formula (II) with methanesulfonic acid or hydrogen chloride, e.g., a mesylate, a dimesylate, a trimesylate, a hydrochloride, a dihydrochloride or a trihydrochloride of the compound of formula (II).

In some embodiments, the compound of formula (II) is Compound 23.

In some embodiments, the pharmaceutically acceptable salt of the compound of formula (II) is selected from the group consisting of 3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide dimesylate (Compound 41);

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide dihydrochloride (Compound 42);

methyl-N-(3-(3-methyl-1H-1,2,4-triazol-1-yl)-5-(trifluoromethyl)phenyl)-3-(2-(pyrazolo[1,5-a]pyrimidin-6-yl)ethynyl)benzamide mesylate (Compound 43);

N-(3-(1H-imidazol-1-yl)-5-(trifluoromethyl)phenyl)-4-methyl-3-(2-(pyrazolo[1,5-a]pyrimidin-6-yl)ethynyl)benzamide mesylate (Compound 44);

3-(2-(2-(cyclopropylamino)pyrimidin-5-yl)ethynyl)-4-methyl-N-(4-((4-methylpiperazin-1-yl)methyl)-3-(trifluoromethyl)phenyl)benzamide trimesylate (Compound 45);

3-(2-(1H-pyrazolo[3,4-b]pyridin-5-yl)ethynyl)-4-methyl-N-(3-(3-methyl-1H-1,2,4-triazol-1-yl)-5-(trifluoromethyl)phenyl)benzamide mesylate (Compound 46);

3-(2-(1H-pyrazolo[3,4-b]pyridin-5-yl)ethynyl)-N-(3-tert-butyl-5-(4-methyl-1H-imidazol-1-yl)phenyl)-4-methylbenzamide mesylate (Compound 47); and, 4-methyl-N-(4-((4-methylpiperazin-1-yl)methyl)-3-(trifluoromethyl)phenyl)-3-(2-(pyrazolo[1,5-a]pyrimidin-6-yl)ethynyl)benzamide dimesylate (Compound 48).

In some embodiments, the pharmaceutically acceptable salt of the compound of formula (II) is Compound 41 or Compound 42.

In some embodiments, the substance M is Compound C, a pharmaceutically acceptable salt thereof or a solvate thereof.

In some embodiments, the substance N is Compound 23, a pharmaceutically acceptable salt thereof or a solvate thereof.

In some embodiments, the substance M is Compound C, a pharmaceutically acceptable salt thereof or a solvate thereof; and, the substance N is Compound 23, a pharmaceutically acceptable salt thereof or a solvate thereof.

In some embodiments, the substance M is Compound C, a pharmaceutically acceptable salt thereof or a solvate thereof; and, the substance N is Compound 41 or a solvate thereof.

In some embodiments, the substance M is Compound C, a pharmaceutically acceptable salt thereof or a solvate thereof; and, the substance N is Compound 42 or a solvate thereof.

In the pharmaceutical combination, the substance M and the substance N can be present in a single pharmaceutical composition, or the substance M and the substance N are separately present in different single pharmaceutical compositions. When the substance M and the substance N must be administrated through different routes of administration or in different frequencies of administration, preferably the substance M and the substance N are separately present in different single pharmaceutical compositions.

In another aspect, the invention also provides a single pharmaceutical composition comprising:

substance M, wherein the substance M is a compound of formula (I), a pharmaceutically acceptable salt thereof or a solvate thereof;

substance N, wherein the substance N is a compound of formula (II), a pharmaceutically acceptable salt thereof or a solvate thereof; and, a pharmaceutical excipient, wherein, the substance M, the substance N, the compound of formula (I) and the compound of formula (II) are as defined above.

In another aspect, the invention also provides a pharmaceutical composition comprising:

a first single pharmaceutical composition comprising substance M and a pharmaceutical excipient, wherein the substance M is a compound of formula (I), a pharmaceutically acceptable salt thereof or a solvate thereof; and, a second single pharmaceutical composition comprising substance N and a pharmaceutical excipient, wherein the substance N is a compound of formula (II), a pharmaceutically acceptable salt thereof or a solvate thereof;

wherein, the substance M, the substance N, the compound of formula (I) and the compound of formula (II) are as defined above.

In another aspect, the invention also provides a kit comprising:

a first container comprising the first single pharmaceutical composition as defined above; and, a second container comprising the second single pharmaceutical composition as defined above.

In another aspect, the invention also provides a use of the combination, the single pharmaceutical composition or the pharmaceutical composition as described above in manufacturing a medicament for preventing and/or treating cancer.

In another aspect, the invention also provides a use of substance M in manufacturing a medicament for preventing and/or treating cancer, wherein the substance M is used in combination with substance N;

the substance M is a compound of formula (I), a pharmaceutically acceptable salt thereof or a solvate thereof;

the substance N is a compound of formula (II), a pharmaceutically acceptable salt thereof or a solvate thereof;

wherein, the substance M, the substance N, the compound of formula (I) and the compound of formula (II) are as defined above.

In another aspect, the invention also provides a use of substance N in manufacturing a medicament for preventing and/or treating cancer, wherein the substance N is used in combination with substance M;

the substance M is a compound of formula (I), a pharmaceutically acceptable salt thereof or a solvate thereof;

the substance N is a compound of formula (II), a pharmaceutically acceptable salt thereof or a solvate thereof;

wherein, the substance M, the substance N, the compound of formula (I) and the compound of formula (II) are as defined above.

In another aspect, the invention provides a method for preventing and/or treating cancer comprising administering to a subject (e.g., a human or a mouse) in need thereof a therapeutically effective amount of substance M and substance N;

the substance M is a compound of formula (I), a pharmaceutically acceptable salt thereof or a solvate thereof;

the substance N is a compound of formula (II), a pharmaceutically acceptable salt thereof or a solvate thereof;

wherein, the substance M, the substance N, the compound of formula (I) and the compound of formula (II) are as defined above.

For all aspects of the invention mentioned above, the cancer includes, but is not limited to, adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, acute lymphocytic leukemia (ALL) in adults, acute myeloid leukemia (AML), chronic lymphocytic leukemia (CLL), chronic myeloid leukemia (CML), chronic myelomonocytic leukemia (CMML), leukemia in children, liver cancer, lung cancer-non-small cell, lung cancer-small cell, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, liposarcoma (e.g., well-differentiated liposarcoma or dedifferentiated liposarcoma), leiomyosarcoma, alveolar and embryonal rhabdomyosarcoma, ovarian cancer, pancreatic cancer, penile cancer, pituitary tumors, prostate cancer, retinoblastoma, rhabdomyosarcoma, salivary gland cancer, sarcoma-adult soft tissue cancer, skin cancer-basal and squamous cell, skin cancer-melanoma, small intestine cancer, stomach cancer, testicular cancer, thymus cancer, thyroid cancer, uterine sarcoma, vaginal cancer, vulvar cancer, Waldenstrom macroglobulinemia, and Wilms tumor.

In some embodiments, the cancer is acute myeloid leukemia.

In some embodiments, the cancer is acute myeloid leukemia with wild type FLT3 gene or mutant FLT3 gene.

In some embodiments, the cancer is acute myeloid leukemia with mutant FLT3 gene comprising a mutation selected from the group consisting of ITD mutation, D835H mutation, D835Y mutation, K663Q mutation, N841I mutation and R834Q mutation.

In some embodiments, the cancer is acute myeloid leukemia with mutant FLT3 gene comprising an ITD mutation.

In some embodiments, the cancer is acute myeloid leukemia with wild type TP53 (tumor protein p53) gene.

In some embodiments, the cancer is acute myeloid leukemia with mutant FLT3 gene comprising an ITD mutation and wild type TP53 gene.

For all aspects of the invention as mentioned above, the administration of the substance M and the substance N can be as described below.

The substance M and the substance N can be administrated simultaneously or separately.

The term "administrated simultaneously" means administration at a same time point, for example, a single pharmaceutical composition comprising both the substance M and the substance N is administrated; or, "a single pharmaceutical composition comprising the substance M" and "a single pharmaceutical composition comprising the substance N" are administered in a same time point.

The term "administrated separately" means administration at different time points, for example, "a single pharmaceutical composition comprising the substance M" and "a single pharmaceutical composition comprising the substance N" are administered separately at different time points; or, for example, one of "a single pharmaceutical composition comprising the substance M" and "a single pharmaceutical composition comprising the substance N" is administered first and the other is subsequently administered. The separated administration may be close in time or distant in time but make sure the substance M and the substance N can act in concert so as to provide the desired therapeutic effect. For example, the substance M can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the substance N, to a subject in need thereof. In some embodiments, the substance M and the substance N are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

Whether the substance M and the substance N are administrated simultaneously or separately, the administration regimens (e.g., route, dose and interval of administration) of the substance M and the substance N can be the same or different, which can be adjusted by a person skilled in the art in order to provide an optimal therapeutic effect as needed.

Suitable routes of administration for the substance M and the substance N includes gastrointestinal administration (e.g., oral administration) and parenteral administration (e.g., injection, e.g., intravenous injection, subcutaneous injection, or intramuscular injection).

Oral administration may involve swallowing, so that the compound enters the gastrointestinal tract, and/or buccal, lingual, or sublingual administration by which the compound enters the blood stream directly from the mouth. Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches. Further, the compound or salts of the invention can be administered as a spray dried dispersion. Solid formulations for oral administration may be formulated to be immediate and/or modified release. Modified release formulations include delayed-, sustained-, pulsed-, controlled-, targeted and programmed release. Liquid formulations include suspensions, solutions, syrups and elixirs. Such formulations may be employed as fillers in soft or hard capsules (made, for example, from gelatin or hydroxypropyl methylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Formulations for parenteral administration may be formulated to be immediate and/or modified release. Modified release formulations include delayed-, sustained-, pulsed-, controlled-, targeted and programmed release. Thus the compounds of the prevent invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic) acid (PGLA) microspheres.

In some embodiments, the substance M, e.g., Compound C, is administered orally.

In some embodiments, the substance N, e.g., Compound 23, Compound 41 or Compound 42, is administered orally.

In some embodiments, the substance M, e.g., Compound C, is administered orally.

In some embodiments, the substance N, e.g., Compound 23, Compound 41 or Compound 42, is administered orally.

The substance M can be administered (e.g., orally or by injection) at a dose based on the body weight of the subject, non-limiting examples of the dose (referred to an amount for one time of administration) can range from 0.01 to 50 mg/kg, e.g., 0.05 mg/kg, 0.1 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 25 mg/kg, 30 mg/kg, 35 mg/kg, 40 mg/kg, 45 mg/kg or 50 mg/kg. In some embodiments, the dose of the substance M is 1-30 mg/kg, e.g., 20-30 mg/kg, e.g., 20 mg/kg or 30 mg/kg.

The above doses of the substance M can be administered to the subject in a frequency of QD (once a day), BID (twice a day), TID (three times a day), Q2D (once every two days), QW (once a week), BIW (twice a week) or Q2W (once every two weeks). In some embodiments, the above doses of the substance M is administered Q2D.

In some embodiments, the substance M, e.g., Compound C, is administered (e.g., orally or by injection) to the subject (e.g., a human or mouse) at a dose of 20 mg/kg, Q2D.

In some embodiments, the substance M, e.g., Compound C, is administered (e.g., orally or by injection) to the subject (e.g., a human or mouse) at a dose of 30 mg/kg, Q2D.

In some embodiments, the substance M, e.g., Compound C, is orally administered to the subject (e.g., a human or mouse) at a dose of 20 mg/kg, Q2D.

In some embodiments, the substance M, e.g., Compound C, is orally administered to the subject (e.g., a human or mouse) at a dose of 30 mg/kg, Q2D.

The substance M can also be administered (e.g., orally or by injection) to the subject in a fixed dose, i.e., a fixed or predetermined dose to the subject. Non-limiting examples of the fixed dose (referred to an amount for one time of administration) can range from 0.1-1000 mg, e.g., 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475 or 500 mg.

The above fixed doses of the substance M can be administrated to the subject in a frequency of QD (once a day), BID (twice a day), TID (three times a day), Q2D (once every two days), QW (once a week), BIW (twice a week) or Q2W (once every two weeks). In some embodiments, the above fixed doses of the substance M is administered Q2D.

The substance N can be administered (e.g., orally or by injection) at a dose based on the body weight of the subject, non-limiting examples of the dose (referred to an amount for one time of administration) can range from 0.01 to 50 mg/kg, e.g., 0.05 mg/kg, 0.1 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 25 mg/kg, 30 mg/kg, 35 mg/kg, 40 mg/kg, 45 mg/kg or 50 mg/kg. In some embodiments, the dose of the substance N is 1-20 mg/kg, e.g., 10 mg/kg.

The above doses of the substance N can be administered to the subject in a frequency of QD (once a day), BID (twice a day), TID (three times a day), Q2D (once every two days), QW (once a week), BIW (twice a week) or Q2W (once every two weeks). In some embodiments, the above doses of the substance N is administered Q2D.

In some embodiments, the substance N, e.g., Compound 23, Compound 41 or Compound 42, is administered to the subject (e.g., a human or mouse) at a dose of 10 mg/kg, Q2D.

In some embodiments, the substance N, e.g., Compound 23, Compound 41 or Compound 42, is orally administrated to the subject (e.g., a human or mouse) at a dose of 10 mg/kg, Q2D.

The substance N can also be administered (e.g., orally or by injection) to the subject in a fixed dose, i.e., a fixed or predetermined dose to the subject. Non-limiting examples of the fixed dose (referred to an amount for one time of administration) can range from 0.1-1000 mg, e.g., 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475 or 500 mg.

The above fixed doses of the substance N can be administrated to the subject in a frequency of QD (once a day), BID (twice a day), TID (three times a day), Q2D (once every two days), QW (once a week), BIW (twice a week) or Q2W (once every two weeks). In some embodiments, the above fixed doses of the substance N is administrated Q2D.

In some embodiments, the substance M (e.g., Compound C) and the substance N (e.g., Compound 23, Compound 41 or Compound 42) can be administrated (e.g., orally or by injection) to a subject in a weight ratio (referred to an amount for one time of administration) of 50:1 to 1:50, e.g., 50:1, 45:1, 40:1, 35:1, 30:1, 25:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:25, 1:30, 1:35, 1:40, 1:45 or 1:50.

In some embodiments, the substance M, e.g., Compound C, is orally administrated to the subject at a dose of 20 mg/kg, Q2D; and, the substance N, e.g., Compound 23, Compound 41 or Compound 42, is orally administrated to the subject at a dose of 10 mg/kg, Q2D.

In some embodiments, the substance M, e.g., Compound C, is orally administrated to the subject at a dose of 30 mg/kg, Q2D; and, the substance N, e.g., Compound 23, Compound 41 or Compound 42, is orally administrated to the subject at a dose of 10 mg/kg, Q2D.

In another aspect, the invention provides a method for inhibiting FLT3 kinase activity in vitro comprising contacting substance N with the FLT3 kinase;

the substance N is a compound of formula (II), a pharmaceutically acceptable salt thereof or a solvate thereof;

wherein, the substance N and the compound of formula (II) are as defined above.

In some embodiments, the FLT3 kinase is a FLT3 kinase encoded by wild type FLT3 gene or mutant FLT3 gene.

In some embodiments, the FLT3 kinase is a FLT3 kinase encoded by mutant FLT3 gene comprising a mutation selected from the group consisting of ITD mutation, D835H mutation, D835Y mutation, K663Q mutation, N841I mutation and R834Q mutation.

In some embodiments, the FLT3 kinase is a FLT3 kinase encoded by mutant FLT3 gene comprising an ITD mutation.

In another aspect, the invention provides a method for inhibiting FLT3 kinase activity comprising administering to a subject in need thereof a therapeutically effective amount of substance N;

the substance N is a compound of formula (II), a pharmaceutically acceptable salt thereof or a solvate thereof;

wherein, the substance N and the compound of formula (II) are as defined above.

The administration of the substance N and the FLT3 kinase can be as defined above.

In another aspect, the invention provides a method for treating acute myeloid leukemia comprising administering to a subject in need thereof a therapeutically effective amount of substance N;

the substance N is a compound of formula (II), a pharmaceutically acceptable salt thereof or a solvate thereof;

wherein, the substance N and the compound of formula (II) are as defined above.

The administration of the substance N can be as defined above.

In some embodiments, the acute myeloid leukemia is acute myeloid leukemia with wild type FLT3 gene or mutant FLT3 gene.

In some embodiments, the acute myeloid leukemia is acute myeloid leukemia with mutant FLT3 gene comprising a mutation selected from the group consisting of ITD mutation, D835H mutation, D835Y mutation, K663Q mutation, N841I mutation and R834Q mutation.

In some embodiments, the acute myeloid leukemia is acute myeloid leukemia with mutant FLT3 gene comprising an ITD mutation.

In another aspect, the invention also provides a use of substance N in manufacturing a FLT3 kinase inhibitor, wherein the substance N is a compound of formula (II), a pharmaceutically acceptable salt thereof or a solvate thereof;

wherein, the substance N and the compound of formula (II) are as defined above. The FLT3 kinase can be as defined above.

In another aspect, the invention also provides a use of substance N in manufacturing a medicament for preventing and/or treating acute myeloid leukemia, wherein the substance N is a compound of formula (II), a pharmaceutically acceptable salt thereof or a solvate thereof;

wherein, the substance N and the compound of formula (II) are as defined above.

The administration of the substance N and the acute myeloid leukemia can be as defined above.

As used herein, the term "alkyl" refers to a linear or branched saturated hydrocarbyl group having an indicated number of carbon atoms, including but not limited to methyl, ethyl, n-propyl, iso-propyl, n-butyl, sec-butyl, tert-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term $C_{m-n}$ means the alkyl group has "m" to "n" carbon atoms. The term "alkylene" refers to an alkyl group having a substituent. When an alkyl group is indicated to be substituted by an indicated substituent (e.g., substituted alkyl, alkyl substituted by), the alkyl group can be substituted by the indicated substituent. The alkyl can be substituted by one or more (e.g., one to three) of the group independently selected from halogen, trifluoromethyl, trifluoromethoxy, hydroxyl, alkoxyl, nitro, cyano, alkylamino, and amino groups.

As used herein, the term "halogen" is defined as fluorine, chlorine, bromine, and iodine.

As used herein, the term "hydroxyl" is defined as —OH.

As used herein, the term "alkoxyl" is defined as —OR, wherein R is alkyl.

As used herein, the term "amino" is defined as —NH$_2$, and the term "alkylamino" is defined as —N(R)$_2$, wherein at least one R is alkyl and the second R is alkyl or hydrogen.

As used herein, the term "carbamoyl" is defined as —C(=O)N(R)$_2$.

As used herein, the term "carboxy" is defined as —C(=O)OH or a salt thereof.

As used herein, the term "nitro" is defined as —NO$_2$.

As used herein, the term "cyano" is defined as —CN.

As used herein, the term "trifluoromethyl" is defined as —CF$_3$.

As used herein, the term "trifluoromethoxy" is defined as —OCF$_3$.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, of the group independently selected from, for example, halogen, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, of the group independently selected from, for example, halogen, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

In certain embodiments, the heteroaryl is a stable monocyclic ring with up to six atoms or a stable bicyclic ring in which each ring contains up to six atoms wherein at least one of the rings is an aromatic ring having 1 to 4 heteroatom(s) independently selected from the group consisting of nitrogen, oxygen and sulfur. Any N-oxidation derivatives of the heteroaryl containing nitrogen atoms are also included in the definition of heteroaryl. When heteroaryl group as a substituent is a bicyclic ring and one of the two rings is non-aromatic or without heteroatom, this bicyclic ring is fused through the aromatic ring or the ring containing heteroatom.

As used herein, the term "cycloalkyl" refers to a monocyclic or bicyclic, saturated or partially unsaturated cyclic hydrocarbyl group having an indicated number (e.g., 3 to 8) of ring carbon atoms, including but is not limited to cyclopropyl, cyclobutyl, cyclopentyl, cyclohexyl, cycloheptyl, and cyclooctyl. The cycloalkyl group can be optionally substituted by one or more (e.g., 1 to 3) of the group independently selected from halogen, trifluoromethyl, trifluoromethoxy, hydroxyl, alkoxyl, nitro, cyano, alkylamino, and amino groups.

As used herein, the term "heterocycloalkyl" refers to a monocyclic or a bicyclic, saturated or partially unsaturated ring system having an indicated number (e.g., 4 to 12) of ring atoms, of which an indicated number (e.g., 1 to 5) of the ring atoms is(are) heteroatom independently selected from the group consisting of nitrogen, oxygen and sulfur, and the remaining ring atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of the group independently selected from halogen, $C_{1-6}$ alkyl, $C_{1-6}$ alkoxy, cyano, amino, carbamoyl, nitro, carboxy, $C_{2-7}$ alkenyl, $C_{2-7}$ alkynyl, and the like on an atom of the ring. The heterocycloalkyl can link to other parts of the molecule via a carbon atom or a heteroatom. The heterocycloalkyl group can be substituted by one or more (e.g., 1 to 3) of the group independently selected from halogen, $C_{1-6}$ alkyl, $C_{1-6}$ alkoxy, cyano, amino, carbamoyl, nitro, carboxy, $C_{2-7}$ alkenyl, $C_{2-7}$ alkynyl, and the like on an atom of the ring.

As used herein, the term "heterocycle" refers to a 5-6 membered aromatic or nonaromatic ring containing 1 to 4 heteroatom(s) independently selected from the group consisting of nitrogen, oxygen and sulfur. "Heterocycle" includes the heteroaryl as mentioned above; it also includes dihydro- and tetrahydro-analogs of the heteroaryl. "Heterocycle" includes, but is not limit to, imidazolyl, indolyl, isothiazolyl, isoxazolyl, oxadiazolyl, oxazolyl, oxetanyl, pyranyl, pyrazinyl, pyrazolyl, pyridazinyl, pyridyl, pyrimidinyl, pyrrolyl, quinazolinyl, tetrazolyl, thiadiazolyl, thiazolyl, thienyl, triazolyl, 1,4-dioxanyl, pyrrolidinyl, dihydro-imidazolyl, dihydro-isoxazolyl, dihydro-isothiazolyl, dihydro-oxadiazolyl, dihydro-oxazolyl, dihydro-pyrazinyl, dihydro-pyrazolyl, dihydro-pyridyl, dihydro-pyrimidinyl, dihydro-pyrrolyl, dihydro-tetrazolyl, dihydro-thiadiazolyl, dihydro-thiazolyl, dihydro-thienyl, dihydro-triazolyl, methylene dioxy-benzophenone acyl, tetrahydrofuranyl, tetrahydrothiophenyl, and their N-oxides etc. The linkage of heterocycle substituent can be achieved through carbon atom or heteroatom. In some embodiments, heterocycle is imidazolyl, pyridyl, 1-pyrrolidone, 2-piperidone, 2-pyrimidone, 2-pyrrolidone, thienyl, oxazolyl, triazolyl, isoxazolyl, etc.

Unless specially mentioned, alkyl, cycloalkyl, aryl, heteroaryl and heterocyclic groups can be substituted or not be substituted. For example, $C_1$-$C_6$ alkyl group can be substituted by one, two, or three substituents independently selected from the group consisting of OH, halogen, alkoxyl, dialkylamino, or heterocyclic ring such as morpholinyl, piperidinyl groups.

In some embodiments, Het may form a 4-7 membered monocyclic ring or a bicyclic ring in which each ring is 4-7 membered through the N atom which connects the Het, and the Het optionally contains 1 or 2 heteroatom(s) independently selected from the group consisting of nitrogen, oxygen and sulfur. The Het can also be optionally substituted by one or more substituents selected from $R_{20}$. The Het includes, but is not limit to the following heterocycle, each of which can be optionally substituted by one or more (preferably one, two or three) substituent(s) selected from $R_{20}$:

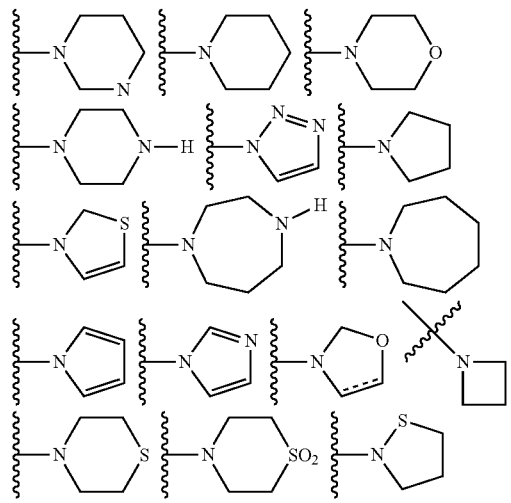

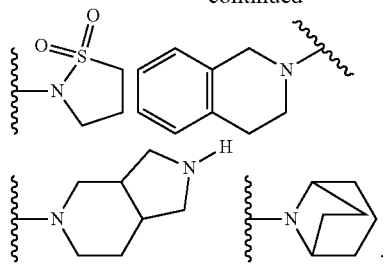

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When a group is indicated to be substituted but the number of the substituent is not provided, it means that the number of the substituent be one or more, e.g., 1-4, e.g., 1, 2, 3 or 4.

The term "pharmaceutically acceptable salt" as used herein refers to a salt formed by a compound and a relatively non-toxic and pharmaceutically acceptable acid or base. When a compound contains a relatively acidic functional group, a base addition salt can be obtained by contacting a sufficient amount of a pharmaceutically acceptable base with the neutral form of the compound in a pure solution or a suitable inert solvent. Examples of pharmaceutically acceptable base addition salts include, but are not limited to, lithium salts, sodium salts, potassium salts, calcium salts, aluminum salts, magnesium salts, zinc salts, bismuth salt, ammonium salts and diethanolamine salts. When a compound contains a relatively basic functional group, an acid addition salt can be obtained by contacting the neutral form of the compound with a sufficient amount of a pharmaceutically acceptable acid in a pure solution or a suitable inert solvent. Examples of pharmaceutically acceptable acids include inorganic acids, wherein the inorganic acids include, but are not limited to, hydrochloric acid, hydrobromic acid, hydroiodic acid, nitric acid, carbonic acid, bicarbonate, phosphoric acid, phosphorous acid, sulfuric acid and the like. Examples of pharmaceutically acceptable acid include organic acids, wherein the organic acids include, but are not limited to, acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, ascorbic acid, gentisic acid, fumaric acid, gluconic acid, formic acid, ethanesulfonic acid, pamoic acid (i.e., 4,4'-methylenebis (3-hydroxy-2-naphthoic acid)), amino acids (such as glutamic acid, arginine) and the like. When a compound contains both a relatively basic functional group and a relatively acidic functional group, it can be converted to a base addition salt or an acid addition salt. The pharmaceutically acceptable salt can be referred to Berge et al., "Pharmaceutical Salts", *Journal of Pharmaceutical Science* 66: 1-19 (1977) or Handbook of Pharmaceutical Salts: Properties, Selection, and Use (P. Heinrich Stahl and Camille G. Wermuth, ed., Wiley-VCH, 2002).

The term "solvate" as used herein refers to a complex formed by the combination of a compound and a stoichiometric or non-stoichiometric solvent. The solvent molecule(s) in the solvate can be present in an ordered or non-ordered arrangement. Examples of the solvents include, but are not limited to, water, methanol, ethanol and the like.

The compound (e.g., the compound of formula (I) or (II), a pharmaceutically acceptable salt thereof and the like) as described herein can exist in an amorphous form or a crystal from. The term "amorphous form" means that the ions or molecules therein are in a disorderly distribution, that is, there is no periodic arrangement between ions and molecules. The term "crystal form" means that the ions or molecules therein are arranged in a strictly periodic manner in three-dimensional space and have a regular pattern of intervals at a certain distance. Due to the difference of the above-mentioned periodic arrangement, there may be various crystal forms, that is, polymorphism.

The compound (e.g., the compound of formula (I) or (II), a pharmaceutically acceptable salt thereof and the like) as described herein, if present as a stereoisomer(s), the stereoisomer(s) can exist as a single stereoisomer or a mixture thereof (e.g., a racemate). The term "stereoisomer" refers to a cis-trans isomer or an optical isomer. These stereoisomers can be isolated, purified and enriched by asymmetric synthesis or chiral separation methods including, but not limited to, thin layer chromatography, rotary chromatography, column chromatography, gas chromatography, high pressure liquid chromatography, or these stereoisomers can be obtained by chiral separation by bonding (e.g., chemical bond) or salting (e.g., physical bond) a compound with another chiral compound. The term "single stereoisomer" refers to the mass content of a certain stereoisomer is not less than 95% in a compound. A typical single stereoisomer is, for example, L-glutamic acid having a purity greater than 98.5%.

The compound (e.g., the compound of formula (I) or (II), a pharmaceutically acceptable salt thereof and the like) as described herein, if present as a tautomer, the tautomer can exist as a single tautomer or a mixture thereof, preferably in a predominantly tautomeric form. For example, acetone and 1-propen-2-ol are typical tautomers of each other.

The atoms contained in the compound (e.g., the compound of formula (I) or (II), a pharmaceutically acceptable salt thereof and the like) as described herein can present in their natural abundance or non-natural abundance. Taking hydrogen atom as an example, its natural abundance means that about 99.985% is protium and about 0.015% is deuterium; its non-natural abundance means that about 95% is deuterium. That is to say, one or more atoms contained in the compound can be present in non-natural abundance. Alternatively, all of the atoms contained in the compound can be present in a natural abundance.

Certain derivatives that can be converted (e.g., by hydrolytic cleavage) into the compound of the invention when administered into the body are also within the scope of the invention. Such derivatives are referred to as 'prodrugs'. Further information on the use of prodrugs may be found in 'Pro-drugs as Novel Delivery Systems, Vol. 14, *ACS Symposium Series* (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in the compounds of the invention with certain moieties known to those skilled in the art as 'pro-moieties' as described, for example, in "Design of Prodrugs" by H Bundgaard (Elsevier, 1985).

Some examples of such prodrugs include:
(i) where the compound contains an alcohol functionality (—OH), an ether thereof, for example, replacement of the hydrogen with $(C_1-C_6)$alkanoyloxymethyl;
(ii) where the compound contains a secondary amino functionality, an amide thereof, for example, replacement of hydrogen with $(C_1-C_{10})$alkanoyl.

The term "pharmaceutical excipient" as used herein refers to an excipient and/or an additive used in producing a medicament or in formulating a formulation, which includes all substances contained in a pharmaceutical preparation except the active ingredient. Examples of the pharmaceutical excipient can be referred to Pharmacopoeia of the People's Republic of China (Volume IV, 2015 edition), or the Handbook of Pharmaceutical Excipients (Raymond C Rowe, 2009 Sixth Edition).

A "therapeutically effective amount" of a compound or a composition refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist. It will be appreciated that the unit content of each active agent contained in an individual dose of each dosage form need not in itself constitute an effective amount since the necessary effective amount can be reached by administration of a plurality of dosage units.

The term "pharmaceutically acceptable" as used herein refers to an acid or a base (used in the preparation of a salt), a solvent, an excipient and the like, which is generally non-toxic, safe, and suitable for a patient. The term "patient" is preferably a mammal, more preferably a human.

The term "preventing" refers to prophylactic administration to healthy patients to prevent the development of the conditions mentioned herein. Moreover, the term "preventing" means prophylactic administration to patients being in a pre-stage of the conditions to be treated.

The term "treating" as used herein refers to therapeutic therapy. When referring to a particular condition, the treating refers to: (1) alleviating one or more of the biological manifestations of a disease or a condition, (2) interfering with (a) one or more points in the biological cascade that leads to a condition or (b) one or more of the biological manifestations of a condition, (3) improving one or more of symptoms, effects or side effects associated with a condition or one or more of the symptoms, effects or side effects associated with a condition or treatment thereof, or (4) slowing the progression of one or more of the biological manifestations of a disorder or a condition.

The term "subject" as used herein refers to any animal that is to be administered or has been administered the compound or composition in accordance with an embodiment of the invention, which is preferably a mammal, more preferably a human. The term "mammal" as used herein includes any mammal. Examples of mammals include, but are not limited to, cows, horses, sheep, pigs, cats, dogs, mice, rats, rabbits, guinea pigs, monkeys and humans. The preferred subject is a human.

The term "FLT3 kinase inhibitor" as used herein refers to a substance that can directly or indirectly reduces, or inhibits, either partially or in full, the activity of FLT3 kinase.

The term "container" as used herein refers to any container suitable for storage, transport, distribution and/or disposal of a pharmaceutical product.

The abbreviations "p.o" (i.e., orally), "q.d" or "QD" (i.e. daily), "q2d" or "Q2D" (i.e., once every two days) and the like are used to describe the route of administration or the dosage regiment in their general meanings.

The use of the terms "a", "an", "the", and similar referents in the context of describing the invention (especially in the context of the claims) are to be construed to cover both the singular and the plural, unless otherwise indicated. The use of any and all examples, or exemplary language (including "e.g.", "such as" and "for example") provided herein, is intended to better illustrate the invention and is not a limitation on the scope of the invention unless otherwise claimed. No language in the specification should be construed as indicating any non-claimed element as essential to the practice of the invention.

The compound of formula (I) and its derivatives (e.g., a pharmaceutically acceptable salt or a solvate) can be synthesized according to WO2015161032A1 (also published as US2015299211A1, EP3131544A1 and so on, all of which are incorporated by reference in their entireties) and common sense in the art.

The compound of formula (II) and its derivatives (e.g., a pharmaceutically acceptable salt or a solvate) can be synthesized according to WO2012000304A1 (also published as EP2594567A1, US2013196985A1 and so on, all of which are incorporated by reference in their entireties) and common sense in the art.

Without violating the common sense in the art, the above preferred conditions can be arbitrarily combined, then preferred embodiments of the invention are obtained.

The reagents and raw materials used in the invention are commercially available.

It has surprisingly been found that, a combination of the substance M and the substance N achieves greater therapeutic effect than substance M and the substance N alone on Human MOLM-13 AML mouse xenograft model.

DETAILED DESCRIPTION OF THE EMBODIMENT

Figure 1:
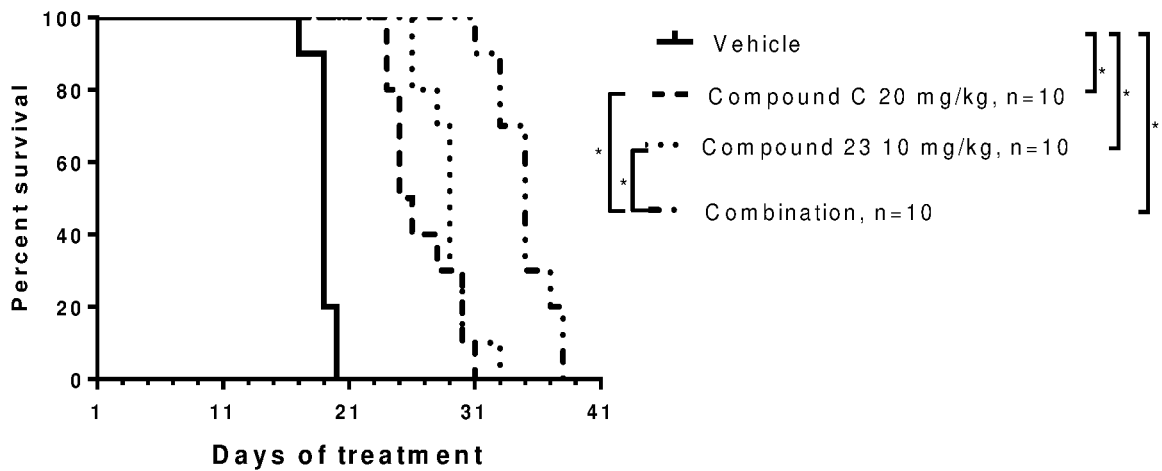
FIG. 1 shows percentage survival of mice in embodiment 5.

The following examples further illustrate the invention, but the invention is not limited thereto.

Embodiment 1. Synthesis of Compound C

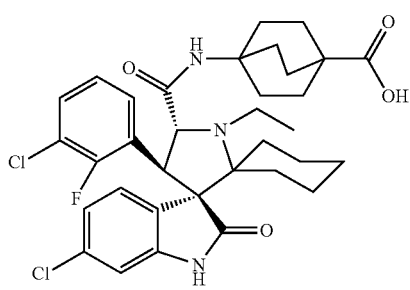

Compound C

Compound C was synthesized according to WO2015161032A1.

Embodiment 2. Synthesis of Compound 23, 3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide

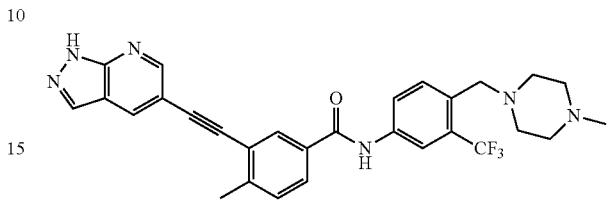

Compound 23 was synthesized according to embodiment 23 of WO2012000304A1.

Embodiment 3. Synthesis of Compound 41, 3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide Dimesylate

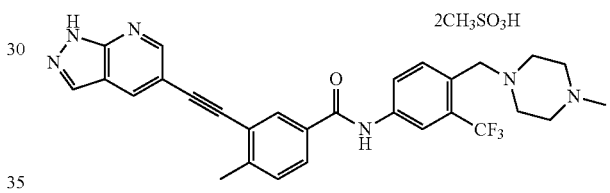

Compound 41 was synthesized according to embodiment 41 of WO2012000304A1.

Embodiment 4. Evaluation of Activity of Compound 23 on Various Type of FLT3 Kinase The kinase assay was conducted using KINOMEscan™. Kinase-tagged T7 phage strains were grown in parallel in 24-well blocks in an $E.\ coli$ host derived from the BL21 strain. $E.\ coli$ were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compound (Compound 23) in 1× binding buffer (20% SeaBlock, 0.17×PBS, 0.05% Tween 20, 6 mM DTT). Test compound were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. The result was shown in Table 1.

TABLE 1

Compound 23 inhibits FLT3 kinases with nanomolar potency

| kinase (gene symbol) | Compound 23 | |
|---|---|---|
| | % Ctrl@10 nM | % Ctrl@100 nM |
| FLT3 (wild type) | 2.4 | 0.75 |
| FLT3 (D835H) | 18 | 2.2 |
| FLT3 (D835Y) | 42 | 17 |
| FLT3 (ITD) | 58 | 2.9 |
| FLT3 (K663Q) | 5 | 0.6 |
| FLT3 (N841I) | 2.9 | 0.05 |
| FLT3 (R834Q) | 23 | 15 |

Note:
The initial screening result for binding is indicated by "% Ctrl". A lower % Ctrl value indicates stronger binding of the compound to the protein.

% Ctrl value=[(test compound signal−positive control signal)/(negative control signal−positive control signal)]×100. Negative control=DMSO (100% Ctrl); positive control=control compound (0% Ctrl).

Embodiment 5. Study of the Combination of Compound C and Compound 23 on Human MOLM-13 AML Mouse Xenograft Model 1.1. Preparation of Test Compound Solution The formulation of Compound C was prepared as homogenous suspension in 0.2% HPMC using a mortar. The drug suspension was prepared every three days or once a week and placed at 4° C. when not in use. Before use, the drug suspension was placed at room temperature and shaken to mix well. The formulation of Compound C was administered to mice via p.o. in a volume of 10 mL/kg.

The formulation of Compound 23 was prepared in 0.2% HPMC in a mortar to generate homogenous suspension. The drug suspension was prepared once every other day and placed at 4° C. when not in use. Before use, the drug suspension was placed at room temperature and shaken well. The formulation of Compound 23 was administered to mice via p.o. in a volume of 10 mL/kg.

1.2. Cell Lines

MOLM-13 cell lines (Human AML cell line MOLM-13 (FLT3-ITD positive and wild type TP53 gene)) were maintained in RPMI-1640 (Cat. C11875500BT, GIBCO) with 10% fetal bovine serum (Cat. 10099-141, GIBCO), 1% L-glutamine, 100 U/mL penicillin G and 100 μg/mL streptomycin (Cat. GNM15140, Hangzhou Geno Biomedical Technology Co., Ltd). Cells were incubated at 37° C. in a humidified incubator with 5% $CO_2$.

1.3. Animals

Six to eight weeks old, female, NOD SCID and BALB/c nude mice were used. Animals were obtained from Vital River Laboratories (VRL, Beijing, China, license number SCXK(J) 2012-0001 and SCXK(J) 2016-0006). The body weights were 17-24 g.

1.4. Animal Housing and Care

Animals were housed in the SPF animal laboratory of Experiment Animal Center in Suzhou GenePharma Co., Ltd. The daily care of animals were conducted by full-time employee of the Experimental Animal Center of GenePharma. Ascentage staff were responsible for conducting the experiments.

1.5. Animal Identification

Each cage was identified by a cage card with the study name, study number, study group, species, and sex. Individual mice were identified by ear tags.

1.6. Randomization

Animals were randomized based on the body weight. However, more than 5 animals were included in each treatment group to minimize the variation between animals.

1.7. Operation and Management Specifications

The protocol and any amendment(s) or procedures involving the care and use of animals in this study were reviewed and approved by the Institutional Animal Care and Use Committee (IACUC) of GenePharma prior to conduct. During the study, the care and use of animals was conducted in accordance with the regulations of the Association for Assessment and Accreditation of Laboratory Animal Care (AAALAC).

1.8. Housing Conditions

Housing: Animals were housed in cages with not more than 5 mice per cage.

Range of daily temperature: 20-26° C.

Range of daily humidity: 40%-70%.

Light: 12 hours on and 12 hours off.

Diet and Water

Radiation-sterilized dry granule food was offered ad libitum during the study period. Autoclaved second-level osmotic water was made freely available from water bottles. Reverse osmosis (RO) water was autoclaved before use. Animals had free access to sterile drinking water.

Bedding

Wood shavings were used for animal bedding, which were sterilized by autoclave before use. Beddings were changed once a week.

Acclimation

Upon arrival, mice were acclimated to the environment for at least three days prior to initiate the study.

1.9. Experimental Procedure

MOLM-13 systemic tumor model were established by injecting tumor cells into the tail vein (10×10$^6$ cells/mouse) under the sterile condition. To establish the MOLM-13 systemic model, all animals were intraperitoneally injected (i.p.) with cyclophosphamide (150 mg/kg) for two consecutive days before the inoculation of MOLM-13 cells. On the third day after cell inoculation, animals were randomized into 10 mice per group and treatment was initiated (day 1) according to Table 2.

TABLE 2

Groups and dosage regimen

| Group | Animals | Treatment | Dose (mg/kg) | Route | Schedule |
|---|---|---|---|---|---|
| 1 | 10 | Vehicle | — | p.o. | q2d × 21 d |
| 2 | 10 | Compound 23 | 10 | p.o. | q2d × 21 d |
| 3 | 10 | Compound C | 20 | p.o. | q2d × 21 d |
| 4 | 10 | Compound 23 | 10 | p.o. | q2d × 21 d |
| | | Compound C | 20 | p.o. | q2d × 21 d |

The animals were euthanized when the experimental animals had symptoms such as weight loss and weight loss greater than 20%, limb paralysis, tumor metastasis to the eye causing ocular protrusion, tumor metastasis to the abdominal cavity causing abdominal enlargement. These severe health issues were considered as the same as animal death caused by tumor growth and the affected animals were sacrificed immediately.

1.10. Results

The date of the last mouse died (the last measurement) was used for analysis of median overall survival and the generation of Kaplan-Meier plots. Survival curves of different treatment groups were compared using log-rank test with Bonferroni's multiple test. All data were analyzed in SPSS version 18.0 (IBM, Armonk, NY, U.S.A.). Prism version 6 (GraphPad Software Inc., San Diego, CA, U.S.A.) was used for graphic presentation.

The results were shown in FIG. 1 (* means P<0.05) and Table 3.

TABLE 3

Median survival time of mice of each group

| Group | Vehicle | Compound C | Compound 23 | Combination |
|---|---|---|---|---|
| Median survival time of mice (days) | 19 | 25.5 | 29 | 35 |
| Prolonged survival time of mice (days) | — | 6.5 | 10 | 16 |

The mice in the vehicle group began to die on the 17th day after the start of treatment (i.e., 19 days after cell inoculation), and all mice died on the 20th day after the start of treatment (i.e., 22 days after cell inoculation), showing a median survival of 19 days. The median survival time of mice of the Compound C group was 25.5 days (P<0.05 compared with the vehicle control group), showing an excellent therapeutic effect. Compound 23 as a single drug also significantly prolonged the survival time of mice, showing a median survival time of 29 days (P<0.05, compared with the vehicle group). The combination of Compound C and Compound 23 further prolonged the survival time of mice, and the median survival time reached 35 days (P<0.05 compared with the vehicle group, compared with the Compound C group or compared with the Compound 23 group).

Embodiment 6. Study of the Combination of Compound C and Compound 23 on Human MV-4-11 AML Mouse Xenograft Model 1.1. Preparation of Test Compound Solution The formulation of Compound C was prepared as homogenous suspension in 0.2% HPMC using a mortar. The drug suspension was prepared every three days or once a week and placed at 4° C. when not in use. Before use, the drug suspension was placed at room temperature and shaken to mix well. The formulation of Compound C was administered to mice via p.o. in a volume of 10 mL/kg.

The formulation of Compound 23 was prepared in 0.2% HPMC in a mortar to generate homogenous suspension. The drug suspension was prepared once every other day and placed at 4° C. when not in use. Before use, the drug suspension was placed at room temperature and shaken well. The formulation of Compound 23 was administered to mice via p.o. in a volume of 10 mL/kg.

1.2. Cell Line

MV-4-11 cells (Human AML cell line MV-4-11 (FLT3-ITD positive and wild type TP53 gene)) were maintained in IMDM (Cat. C12440500BT, GIBCO), with 10% fetal bovine serum (Cat. 10099-141, GIBCO), 1% L-glutamine, 100 U/mL penicillin G and 100 µg/mL streptomycin (Cat. GNM15140, Hangzhou Geno Biomedical Technology Co., Ltd). Cells were incubated at 37° C. in a humidified incubator with 5% $CO_2$.

1.3. Animals

Six to eight weeks old, female, NOD SCID and BALB/c nude mice were used. Animals were obtained from Vital River Laboratories (VRL, Beijing, China, license number SCXK(J) 2012-0001 and SCXK(J) 2016-0006). The body weights were 17-24 g.

1.4. Animal Housing and Care

Animals were housed in the SPF animal laboratory of Experiment Animal Center in Suzhou GenePharma Co., Ltd. The daily care of animals were conducted by full-time employee of the Experimental Animal Center of GenePharma.

1.5. Animal Identification

Each cage was identified by a cage card with the study name, study number, study group, species, and sex. Individual mice were identified by ear tags.

1.6. Randomization

Randomization was conducted when the size of xenograft tumors reached 100-150 $mm^3$. Based on the size of the tumor and body weight, animals were randomly assigned into experimental groups. Difference between mean tumor volume of each group and mean tumor volume of all test animals did not exceed ±10%.

1.7. Operation and Management Specifications

The protocol and any amendment(s) or procedures involving the care and use of animals in this study were reviewed and approved by the Institutional Animal Care and Use Committee (IACUC) of GenePharma prior to conduct. During the study, the care and use of animals was conducted in accordance with the regulations of the Association for Assessment and Accreditation of Laboratory Animal Care (AAALAC).

1.8. Housing Conditions

Housing: Animals were housed in cages with not more than 5 mice per cage.

Range of daily temperature: 20-26° C.

Range of daily humidity: 40%-70%.

Light: 12 hours on and 12 hours off.

Diet and Water

Radiation-sterilized dry granule food was offered ad libitum during the study period. Autoclaved second-level osmotic water was made freely available from water bottles. Reverse osmosis (RO) water was autoclaved before use. Animals had free access to sterile drinking water.

Bedding

Wood shavings were used for animal bedding, which were sterilized by autoclave before use. Beddings were changed once a week.

Acclimation

Upon arrival, mice were acclimated to the environment for at least three days prior to initiate the study.

1.9. Experimental Procedure

MV-4-11 subcutaneous xenograft models were established by subcutaneously injecting tumor cells ($1\times10^7$ cells (50% Matrigel)/mouse) into the right flank of the mouse under the sterile condition. When the tumors reached an appropriate size (100-200 $mm^3$), mice were randomized into 6 mice per group and treatment was initiated (day 1) according to Table 4.

TABLE 4

Groups and dosage regimen

| Group | Animals | Treatment | Dose (mg/kg) | Route | Schedule |
|---|---|---|---|---|---|
| 1 | 6 | Vehicle | — | p.o. | q2d × 22 d |
| 2 | 6 | Compound 23 | 10 | p.o. | q2d × 22 d |
| 3 | 6 | Compound C | 30 | p.o. | q2d × 22 d |
| 4 | 6 | Compound 23 | 10 | p.o. | q2d × 22 d |
|   |   | Compound C | 30 | p.o. | q2d × 22 d |

The tumors sizes and animal body weights were measured twice a week. Tumor volumes were estimated from measurements of two diameters of the individual tumors as follows:

Tumor Volume (mm$^3$)=$(a \times b^2)/2$

Relative tumor volume (RTV) were calculated according to the follows:

RTV=$V_t/V_1$ where $V_1$ and $V_t$ were respectively the average tumor volume on the first day of treatment (day 1) and the average tumor volume on a certain time point (day T).

Standard NCI procedures were used to calculate tumor parameters (Teicher, B. A. (2011). "Tumor Models in Cancer Research." Second Edition, Human Press). Percent tumor growth inhibition (% T/C) was calculated as the mean RTV of treated tumors (T) divided by the mean RTV of control tumors (C)×100%. The percentage T/C value is an indication of antitumor effectiveness: a value of T/C<42% is considered significant antitumor activity by the NCI. A T/C value <10% is considered to indicate highly significant antitumor activity, and is the level used by the NCI to justify a clinical trial if toxicity and certain other requirements are met (termed DN-2 level activity). A body weight loss (mean of group) of greater than 20%, or greater than 20% of drug deaths are considered to indicate an excessively toxic dosage.

The synergistic analysis was performed using the following formula described in Clarke R. Issues in experimental design and endpoint analysis in the study of experimental cytotoxic agents in vivo in breast cancer and other models [J]. *Breast Cancer Research & Treatment*, 1997, 46(2-3): 255-278, which is incorporated by reference in its entirety: expected value=(A/C)×(B/C); actual value=(AB)/C; A: RTV of drug A; B: RTV of drug B; C=RTV of the vehicle control group; AB=RTV of the combination group. Ratio=expected/actual value. A ratio >1 indicates that the two drugs have a synergistic effect. A ratio=1 indicates the two drugs have additive effects. A ratio <1 indicates the two drugs may have antagonist effects.

According to the earlier publication (Gao, H., et al. (2015). "High-throughput screening using patient-derived tumor xenografts to predict clinical trial drug response" *Nat Med* 21: 1318), additional measurements of response included stable disease (SD), partial tumor regression (PR), and complete regression (CR) were determined by comparing tumor volume change at day t to its baseline: tumor volume change (%)=$(V_t-V_1)/V_1$. The best response was the minimum value of tumor volume change (%) for t≥10. For each time t, the average of tumor volume change from t=1 to t was also calculated. Best average response was defined as the minimum value of this average for t≥10. The criteria for response (mRECIST) were adapted from RECIST criteria (Gao, H., et al. (2015). "High-throughput screening using patient-derived tumor xenografts to predict clinical trial drug response" *Nat Med* 21: 1318; Therasse, P., et al. (2000). "New Guidelines to Evaluate the Response to Treatment in Solid Tumors" *J Natl Cancer Inst* 92(3): 205-216) and defined as follows: mCR, best response <−95% and best average response <−40%; mPR, best response <−50% and best average response <−20%; mSD, best response <35% and Best average response <30%; mPD, not otherwise categorized. SD, PR, and CR were considered responders and used to calculate response rate (%). Body weight of animals were monitored simultaneously. The change in body weight was calculated based on the animal weight of the first day of dosing (day 1). Tumor volume and changes in body weight (%) were represented as the mean±standard error of the mean (SEM).

1.10. Results

One-way ANOVA followed by Games-Howell's post-test was applied to assess the statistical significance of differences between multiple treatment groups. All data were analyzed in SPSS version 18.0 (IBM, Armonk, NY, U.S.A.). Prism version 6 (GraphPad Software Inc., San Diego, CA, U.S.A.) was used for graphic presentation.

Figure 2:
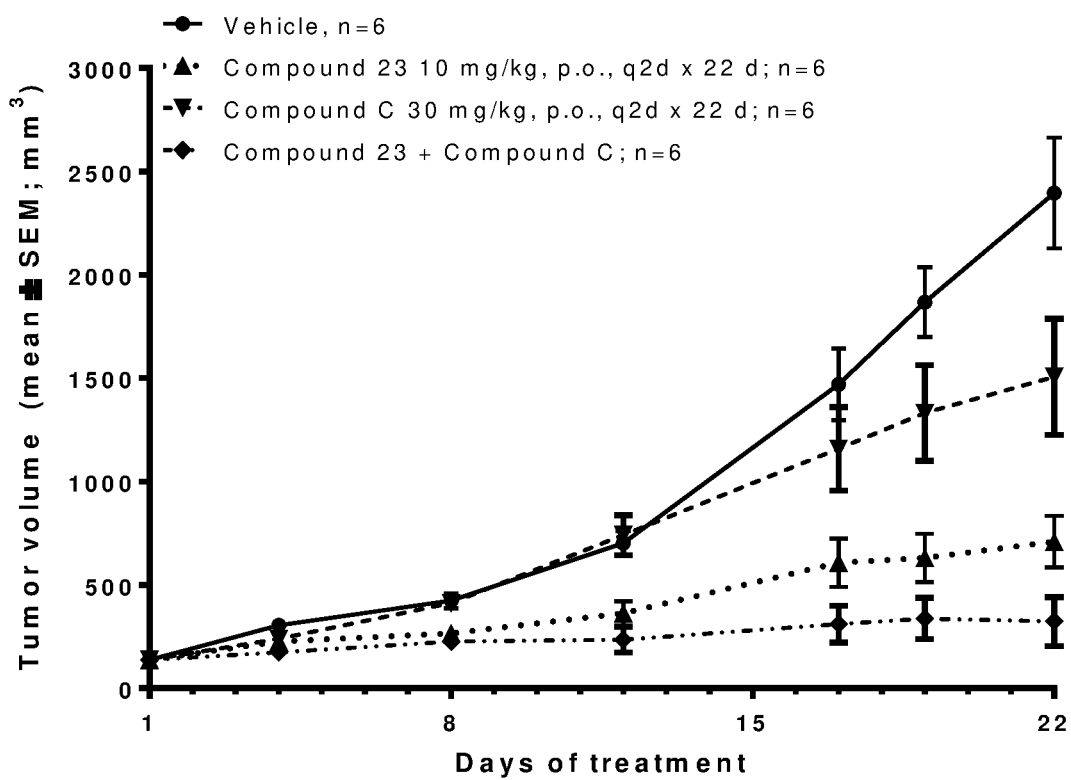
FIG. 2 shows tumor growth curves in embodiment 6.

Tumor growth curves were plotted with the treatment duration (i.e., days) on the X-axis and corresponding tumor volume (geometric mean) on the Y-axis, which was shown in FIG. 2.

Figure 3:
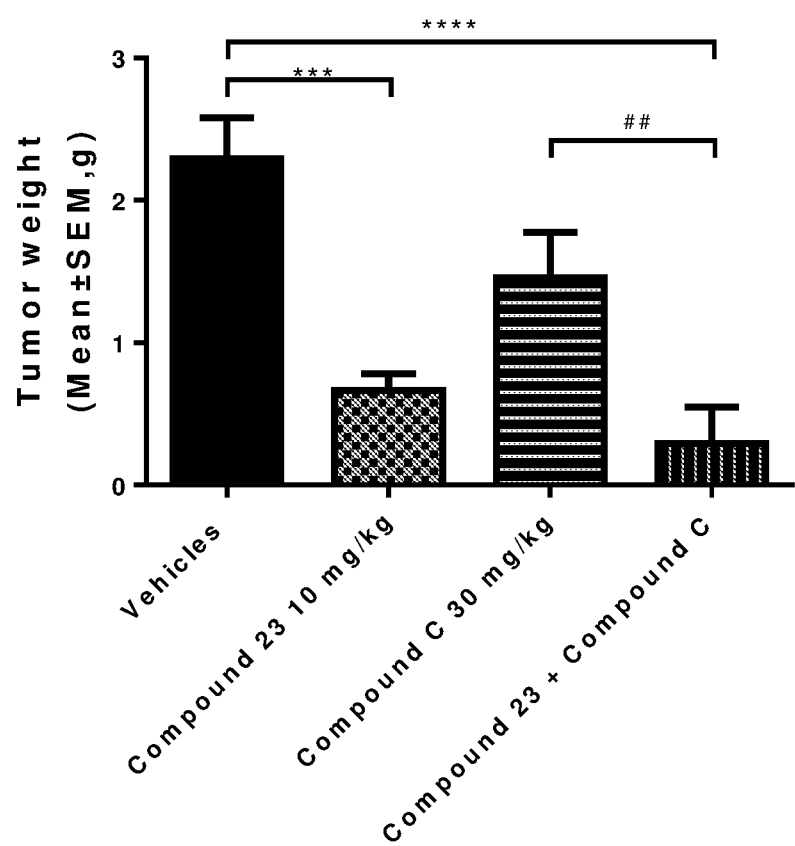
FIG. 3 shows tumor weight on the day 22 in embodiment 6.

The tumor weight on day 22 was shown in Table 5 and FIG. 3.

TABLE 5

Tumor weight on the day 22

| Treatment | Tumor weight on D 22 (Mean ± SEM) |
|---|---|
| Vehicle control | 2.29 ± 0.29 |
| Compound 23 10 mg/kg | 0.67 ± 0.11*** |
| Compound C 30 mg/kg | 1.45 ± 0.32 |
| Compound 23 + Compound C | 0.29 ± 0.10****## |

***P < 0.001,
****P < 0.0001 versus vehicle control;
P < 0.01 versus Compound C monotherapy.

The result of RTV, T/C (%) values, synergy scores and response rate on the day 22 was shown in Table 6.

TABLE 6

RTV, T/C (%) values, synergy scores and response rate on the day 22

| Treatment | RTV@ D 22 | T/C(%)@ D 22 | Synergy @ D 22 | Response rate @ D 22 |
|---|---|---|---|---|
| Vehicle | 18.2 ± 3.3 | — | — | — |
| Compound 23 10 mg/kg | 5.2 ± 0.9 | 28.6 | — | — |
| Compound C 30 mg/kg | 10.8 ± 1.6 | 59.6 | — | — |
| Compound 23 10 mg/kg + Compound C 30 mg/kg | 2.4 ± 0.9*# | 13.4 | 1.27 | — |

*p < 0.05;
p < 0.05 vs. Compound C 30 mg/kg group;
Ratio > 1, Synergistic;
Ratio = 1, Additive;
Ratio < 1, Antagonistic Synergistic effect between Compound C and Compound 23 was demonstrated as synergy score was larger than 1 in the treatment group of Compound 23 10 mg/kg+Compound C 30 mg/kg.

It is to be understood that the foregoing description of the preferred embodiments is intended to be purely illustrative of the principles of the invention, rather than exhaustive thereof, and that changes and variations will be apparent to those skilled in the art, and that the invention is not intended to be limited other than expressly set forth in the following claims.

The invention claimed is:

1. A method for treating acute myeloid leukemia in a subject, the method comprising administering to the subject in need thereof a therapeutically effective amount of substance M and substance N, wherein the substance M is

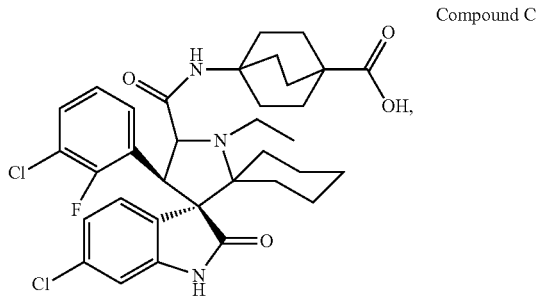 [SMILES: CCN1C(C(=O)NC23CCC(C(=O)O)(CC2)CC3)[C@H](c2cccc(Cl)c2F)[C@]2(C(=O)Nc3cc(Cl)ccc32)C12CCCCC2]

Compound C or a pharmaceutically acceptable salt thereof; and the substance N is

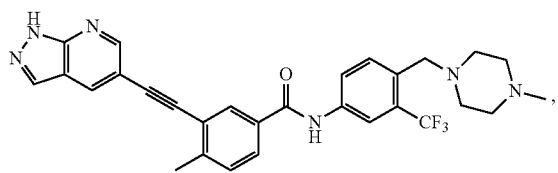 [SMILES: Cc1ccc(C(=O)Nc2ccc(CN3CCN(C)CC3)c(C(F)(F)F)c2)cc1C#Cc1cnc2[nH]ncc2c1]

or a pharmaceutically acceptable salt thereof.

2. The method of claim 1, wherein the substance N is

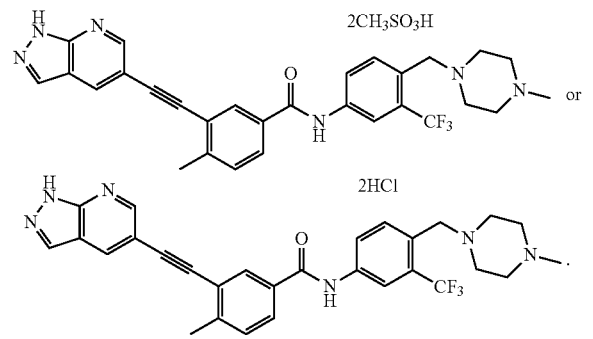

3. The method of claim 1, wherein the substance M is formulated in a first composition, wherein the substance N is formulated in a second composition.

4. The method of claim 3, wherein the substance N is

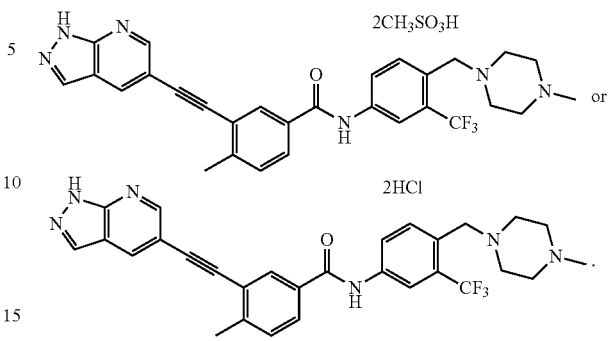

5. The method of claim 1, wherein the method comprises a kit comprising:
   a first container comprises a first pharmaceutical composition comprising the substance M; and,
   a second container comprises a second pharmaceutical composition comprising a the substance N.

6. The method of claim 5, wherein the substance N is

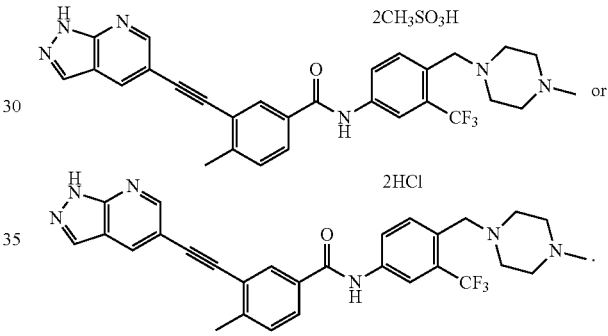

7. The method of claim 1, wherein the acute myeloid leukemia is acute myeloid leukemia with wild type FLT3 gene or mutant FLT3 gene; acute myeloid leukemia with mutant FLT3 gene comprising a mutation selected from the group consisting of ITD mutation, D835H mutation, D835Y mutation, K663Q mutation, N841I mutation and R834Q mutation; and acute myeloid leukemia with mutant FLT3 gene comprising an ITD mutation and wild type TP53 gene.

8. The method of claim 1, wherein the substance M and the substance N are independently administrated orally or parenterally.

9. The method of claim 1, wherein the substance M and the substance N are administrated simultaneously.

10. The method of claim 1, wherein the substance M and the substance N are administrated sequentially.

11. The method of claim 8, wherein parenteral administration comprises intravenous injection, subcutaneous injection, or intramuscular injection.

12. The method of claim 1, wherein, the substance M is administered at a dose based on the body weight of the subject, wherein the dose is 0.01 to 50 mg/kg; wherein the doses of the substance M is administered to the subject in a frequency of QD, BID, TID, Q2D, QW, BIW or Q2W; or
   wherein the substance M is administered to the subject in a fixed dose to the subject, wherein the fixed dose is 0.1-1000 mg, e.g.; wherein the fixed doses of the substance M is administrated to the subject in a frequency of QD, BID, TID, Q2D, QW, BIW or Q2W.

13. The method of claim 1, wherein the substance N is administered at a dose based on the body weight of the subject, wherein the dose is 0.01 to 50 mg/kg, e.g.; wherein the doses of the substance N is administered to the subject in a frequency of QD, BID, TID, Q2D, QW, BIW or Q2W; or wherein the substance N is administered to the subject in a fixed dose, wherein the fixed dose is 0.1-1000 mg, e.g.;
  wherein the fixed doses of the substance N is administrated to the subject in a frequency of QD, BID, TID, Q2D, QW, BIW or Q2W.

14. The method of claim 1, wherein the substance M and the substance N are administrated in a weight ratio of 50:1 to 1:50.

15. The method of claim 14, wherein the substance M and the substance N are administrated in a weight ratio of 50:1, 45:1, 40:1, 35:1, 30:1, 25:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:25, 1:30, 1:35, 1:40, 1:45 or 1:50.

16. The method of claim 14, wherein the substance M and the substance N are administrated in a weight ratio of 2:1 to 3:1.

17. The method of claim 12, wherein, the substance M is administered at a dose based on the body weight of the subject, wherein the dose is 10 to 50 mg/kg.

18. The method of claim 12, wherein the dose is 0.05 mg/kg, 0.1 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 25 mg/kg, 30 mg/kg, 35 mg/kg, 40 mg/kg, 45 mg/kg or 50 mg/kg; or wherein the fixed dose is 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475 or 500 mg.

19. The method of claim 13, wherein the substance N is administered at a dose based on the body weight of the subject, wherein the dose is 8 to 20 mg/kg.

20. The method of claim 13, wherein the dose is 0.05 mg/kg, 0.1 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 25 mg/kg, 30 mg/kg, 35 mg/kg, 40 mg/kg, 45 mg/kg or 50 mg/kg; or wherein the fixed dose is 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475 or 500 mg.

* * * * *